US008436189B2

(12) United States Patent
Nising et al.

(10) Patent No.: US 8,436,189 B2
(45) Date of Patent: *May 7, 2013

(54) HETEROCYCLIC ALKANOL DERIVATIVES

(75) Inventors: Carl Friedrich Nising, Langenfeld (DE); Hendrik Helmke, Liederbach (DE); Pierre Cristau, Lyons (FR); Gorka Peris, Köln (DE); Tomoki Tsuchiya, Düsseldorf (DE); Pierre Wasnaire, Düsseldorf (DE); Jürgen Benting, Leichlingen (DE); Peter Dahmen, Neuss (DE); Ulrike Wachendorff-Neumann, Neuwied (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/117,689

(22) Filed: May 27, 2011

(65) Prior Publication Data
US 2012/0004102 A1 Jan. 5, 2012

Related U.S. Application Data

(60) Provisional application No. 61/350,514, filed on Jun. 2, 2010.

(30) Foreign Application Priority Data

May 27, 2010 (EP) ..................................... 10164141

(51) Int. Cl.
*A61K 31/426* (2006.01)
*C07D 277/24* (2006.01)

(52) U.S. Cl.
USPC ............................ 548/202; 548/203; 514/365

(58) Field of Classification Search .................. 548/202, 548/203
See application file for complete search history.

(56) References Cited

U.S. PATENT DOCUMENTS

| 4,245,432 | A |   | 1/1981 | Dannelly |         |
|-----------|---|---|--------|----------|---------|
| 4,272,417 | A |   | 6/1981 | Barke et al. | |
| 4,618,619 | A |   | 10/1986 | Regel et al. | |
| 4,808,430 | A |   | 2/1989 | Kouno | |
| 5,057,529 | A | * | 10/1991 | Wilson et al. | 514/365 |
| 5,853,973 | A |   | 12/1998 | Kakefuda et al. | |
| 5,876,739 | A |   | 3/1999 | Turnblad et al. | |
| 6,057,353 | A |   | 5/2000 | Jautelat et al. | |
| 2002/0019527 | A1 | * | 2/2002 | Wang et al. | 544/360 |
| 2002/0115564 | A1 |   | 8/2002 | Asrar et al. | |
| 2002/0134012 | A1 |   | 9/2002 | Ding et al. | |
| 2003/0176428 | A1 |   | 9/2003 | Schneidersmann et al. | |
| 2007/0061917 | A1 |   | 3/2007 | McCutchen et al. | |
| 2009/0238798 | A1 |   | 9/2009 | Bogdanova et al. | |
| 2012/0004101 | A1 | * | 1/2012 | Nising et al. | 504/101 |
| 2012/0035051 | A1 | * | 2/2012 | Nising et al. | 504/101 |
| 2012/0065062 | A1 | * | 3/2012 | Nising et al. | 504/101 |
| 2012/0108423 | A1 |   | 5/2012 | Nising et al. | |

FOREIGN PATENT DOCUMENTS

| EP | 0 395 175 A2 | 10/1990 |
| EP | 0 409 418 A1 | 1/1991 |
| WO | WO 96/33270 A1 | 10/1996 |
| WO | WO 02/28186 A2 | 4/2002 |
| WO | WO 02/080675 A1 | 10/2002 |
| WO | WO 2007/024782 A2 | 3/2007 |
| WO | WO 2007/027777 A2 | 3/2007 |

OTHER PUBLICATIONS

Draber, W. and Wegler, R., "Natürliche Pflanzenwuchsstoffe—Phytohormone: 2. Gibberelline," in *Chemie der Pflanzenschutz—und Schädlingsbekämpfungsmittel*, vol. 2, Wegler, R., ed., pp. 401-412, Springer-Verlag, Germany (1970).
English language translation of Draber, W. and Wegler, R., "Natürliche Pflanzenwuchsstoffe—Phytohormone: 2. Gibberelline," in *Chemie der Pflanzenschutz-und Schädlingsbekämpfungsmittel*, vol. 2, Wegler, R., ed., pp. 401-412, Springer-Verlag, Germany (1970).
Rüffer, T., et al., "Thiomethylmagnesium Chlorides: Synthesis via Hg-Mg Transmetallation and Crystallization of a Grignard Compound as 1/1 Adduct of $[Mg(CH_2SPh)_2(thf)_3]$ and $[MgCl_2(thf)_4]$," *Z. Anorg. Allg. Chem.* 627:2408-2412, Wiley-VCH Verlag GmbH, Germany (2001).
International Search Report for International Application No. PCT/EP2011/058437, European Patent Office, Netherlands, mailed Jun. 27, 2011.
Office Action mailed Apr. 5, 2012, in U.S. Appl. No. 13/117,723, inventors Nising, C.F., et al., filed May 27, 2011.
Office Action mailed Apr. 6, 2012, in U.S. Appl. No. 13/117,708, inventors Nising, C.F., et al., filed May 27, 2011.
Office Action mailed Jun. 29, 2012, in U.S. Appl. No. 13/117,653, inventors Nising, C.F., et al., filed May 27, 2011.
Office Action mailed Oct. 17, 2012, in U.S. Appl. No. 13/117,708, inventors Nising, C.F., et al., filed May 27, 2011.
Office Action mailed Nov. 26, 2012, in U.S. Appl. No. 13/117,678, inventors Nising, C.F., et al., filed May 27, 2011.

* cited by examiner

*Primary Examiner* — Laura L. Stockton
(74) *Attorney, Agent, or Firm* — Sterne, Kessler, Goldstein & Fox P.L.L.C.

(57) ABSTRACT

The present invention relates to novel heterocyclic alkanol derivatives, to processes for preparing these compounds, to compositions comprising these compounds and to their use as biologically active compounds, in particular for controlling harmful microorganisms in crop protection and in the protection of materials and as plant growth regulators.

11 Claims, No Drawings

HETEROCYCLIC ALKANOL DERIVATIVES

The present invention relates to novel heterocyclic alkanol derivatives, to processes for preparing these compounds, to compositions comprising these compounds, and to the use thereof as biologically active compounds, especially for control of harmful microorganisms in crop protection and in the protection of materials and as plant growth regulators.

It is already known that particular heterocyclic alkanol derivatives can be used in crop protection as fungicides and/or growth regulators (cf. EP-A 0 395 175, EP-A 0 409 418).

Since the ecological and economic demands made on modern active ingredients, for example fungicides, are increasing constantly, for example with respect to activity spectrum, toxicity, selectivity, application rate, formation of residues and favourable manufacture, and there can also be problems, for example, with resistances, there is a constant need to develop novel fungicidal compositions which have advantages over the known compositions at least in some areas.

Novel heterocyclic alkanol derivatives of the formula (I)

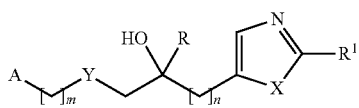

(I)

have now been found, in which
X is O or S,
Y is O, —$CH_2$— or a direct bond,
m is 0 or 1,
n is 0 or 1,
R is in each case optionally substituted alkyl, alkenyl, cycloalkyl or aryl,
$R^1$ is hydrogen, SH, alkylthio, alkoxy, halogen, haloalkyl, haloalkylthio, haloalkoxy, cyano, nitro or Si(alkyl)$_3$,
A is in each case di-Z-substituted phenyl or naphthyl, where the two substituents Z are identical or different,
Z is halogen, cyano, nitro, OH, SH, C(alkyl)(=NOalkyl), $C_3$-$C_7$-cycloalkyl, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, formyl, $C_2$-$C_5$-alkylcarbonyl, $C_2$-$C_5$-haloalkylcarbonyl, $C_2$-$C_5$-alkoxycarbonyl, $C_2$-$C_5$-haloalkoxycarbonyl, $C_3$-$C_6$-alkenyloxy, $C_3$-$C_6$-alkynyloxy, $C_2$-$C_5$-alkylcarbonyloxy, $C_2$-$C_5$-haloalkylcarbonyloxy, trialkylsilyl, or in each case optionally halogen-, $C_1$-$C_4$-alkyl-, $C_1$-$C_4$-alkoxy- or $C_2$-$C_4$-alkylcarbonyl-monosubstituted phenyl, phenoxy or phenylthio,
and the agrochemically active salts thereof.

The salts obtainable in this way likewise have fungicidal and/or plant growth-regulating properties.

The heterocyclic alkanol derivatives usable in accordance with the invention are defined in general terms by the formula (I). Preferred radical definitions for the formulae specified above and below are given below. These definitions apply equally to the end products of the formula (I) and to all intermediates (see also below under "Illustrations of the processes and intermediates").

X is preferably S.
X is likewise preferably O.
Y is preferably O.
Y is likewise preferably —$CH_2$—.
Y is likewise preferably a direct bond.
Y is more preferably O.
Y is likewise more preferably —$CH_2$—.
m is preferably 0.
m is likewise preferably 1.
n is preferably 0.
n is likewise preferably 1.
R is preferably in each case optionally branched $C_3$-$C_7$-alkyl, $C_1$-$C_8$-haloalkyl, $C_2$-$C_7$-alkenyl, $C_2$-$C_7$-haloalkenyl, optionally halogen-, $C_1$-$C_4$-alkyl-, $C_1$-$C_4$-alkoxy-, $C_1$-$C_4$-haloalkoxy-, $C_1$-$C_4$-haloalkylthio- or $C_1$-$C_4$-alkylthio-substituted $C_3$-$C_7$-cycloalkyl, and optionally mono- to tri-halogen- or —$C_1$-$C_4$-alkyl-substituted phenyl.
R is more preferably in each case optionally branched $C_3$-$C_5$-alkyl, $C_1$-$C_6$-haloalkyl, $C_3$-$C_5$-alkenyl, $C_3$-$C_5$-haloalkenyl, optionally halogen-, $C_1$-$C_4$-alkyl-, $C_1$-$C_4$-haloalkyl-, $C_1$-$C_4$-haloalkoxy-, $C_1$-$C_4$-alkoxy-, $C_1$-$C_4$-haloalkylthio- or $C_1$-$C_4$-alkylthio-substituted $C_3$-$C_6$-cycloalkyl.
R is most preferably tert-butyl, isopropyl, 1-chlorocyclopropyl, 1-fluorocyclopropyl, 1-methylcyclopropyl, 1-methoxycyclopropyl, 1-methylthiocyclopropyl, 1-trifluoromethylcyclopropyl, (3E)-4-chloro-2-methylbut-3-en-2-yl, $C_1$-$C_4$-haloalkyl.
$R^1$ is preferably hydrogen, SH, $C_1$-$C_4$-alkylthio, $C_1$-$C_4$-alkoxy or halogen.
$R^1$ is more preferably hydrogen, SH, methylthio, ethylthio, methoxy, ethoxy, fluorine, chlorine, bromine or iodine.
A is preferably di-Z-substituted phenyl, where the two substituents Z are identical or different.
A is more preferably 2- and 4-Z-substituted phenyl, where the two substituents Z are identical or different.
A is likewise more preferably 3- and 4-Z-substituted phenyl, where the two substituents Z are identical or different.
A is likewise more preferably 3- and 5-Z-substituted phenyl, where the two substituents Z are identical or different.
A is preferably di-Z-substituted naphthyl, where the two substituents Z are identical or different.
A is more preferably di-Z-substituted 1-naphthyl, where the two substituents Z are identical or different.
A is likewise more preferably di-Z-substituted 2-naphthyl, where the two substituents Z are identical or different.
Z is preferably halogen, cyano, nitro, C(($C_1$-$C_5$-alkyl)(=NO($C_1$-$C_5$-alkyl)), $C_3$-$C_6$-cycloalkyl, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_2$-$C_4$-alkenyl, $C_2$-$C_4$-alkynyl, $C_1$-$C_4$-alkylsulphinyl, $C_1$-$C_4$-alkylsulphonyl, $C_2$-$C_5$-alkylcarbonyl, $C_2$-$C_5$-alkoxycarbonyl, $C_3$-$C_6$-alkenyloxy, $C_3$-$C_6$-alkynyloxy, $C_2$-$C_5$-alkylcarbonyloxy, or in each case optionally halogen-, $C_1$-$C_4$-alkyl-, $C_1$-$C_4$-haloalkyl-, $C_1$-$C_4$-alkoxy- or $C_2$-$C_4$-alkylcarbonyl-monosubstituted phenyl, phenoxy or phenylthio.
Z is more preferably halogen, cyano, nitro, C($C_1$-$C_4$-alkyl)(=NO($C_1$-$C_4$-alkyl)), $C_3$-$C_6$-cycloalkyl, $C_1$-$C_4$-alkyl, $C_1$-$C_2$-haloalkyl, $C_1$-$C_2$-alkoxy, $C_1$-$C_2$-haloalkoxy, $C_1$-$C_2$-alkylthio, $C_1$-$C_2$-haloalkylthio, $C_1$-$C_2$-alkylsulphinyl, $C_1$-$C_2$-alkylsulphonyl, acetyl, methoxycarbonyl, ethoxycarbonyl, methylcarbonyloxy, or in each case optionally halogen-, $C_1$-$C_2$-alkyl-, $C_1$-$C_2$-haloalkyl-, $C_1$-$C_2$-alkoxy-, acetyl-monosubstituted phenyl, phenoxy or phenylthio.
Z is most preferably fluorine, chlorine, bromine, iodine, cyano, nitro, CH(=NOMe), cyclopropyl, cyclobutyl, cyclopentyl, cyclohexyl, methyl, ethyl, n-propyl, isopropyl, n-, i-, s- or t-butyl, trifluoromethyl, trichloromethyl, difluoromethyl, dichloromethyl, difluorochloromethyl, methoxy, trifluoromethoxy, difluoromethoxy, methylthio, trifluoromethylthio, difluoromethylthio, or in each case optionally fluorine-, chlorine-, bromine-, iodine-, methyl-, ethyl-, trifluoromethyl-, trichloromethyl-, difluoromethyl-, dichloromethyl-, difluorochloromethyl-, methoxy-, acetyl-monosubstituted phenyl, phenoxy or phenylthio.

The radical definitions and explanations given above in general terms or stated within preferred ranges can, however, also be combined with one another as desired, i.e. including between the particular ranges and preferred ranges. They apply both to the end products and correspondingly to precursors and intermediates. In addition, individual definitions may not apply.

Preference is given to those compounds of the formula (I) in which each of the radicals have the above-mentioned preferred definitions.

Particular preference is given to those compounds of the formula (I) in which each of the radicals have the above-mentioned more preferred definitions.

Very particular preference is given to those compounds of the formula (I) in which each of the radicals have the above-mentioned most preferred definitions.

Preference is also given to compounds of the formula (I) in which Y is oxygen.

Preference is also given to compounds of the formula (I) in which Y is —$CH_2$—.

Preference is also given to compounds of the formula (I) in which Y is a direct bond.

Preference is also given to compounds of the formula (I) in which R is t-butyl.

Preference is also given to compounds of the formula (I) in which R is 1,3-difluoro-2-methylpropan-2-yl.

Preference is also given to compounds of the formula (I) in which R is 1-methylcyclopropyl.

Preference is also given to compounds of the formula (I) in which R is 1-fluorocyclopropyl.

Preference is also given to compounds of the formula (I) in which R is 1-chlorocyclopropyl.

Preference is also given to compounds of the formula (I) in which R is isopropyl.

Preference is also given to compounds of the formula (I) in which R is 1-methylcyclohexyl.

Preference is also given to compounds of the formula (I) in which n is 0.

Preference is also given to compounds of the formula (I) in which n is 1.

Preference is also given to compounds of the formula (I) in which X is sulphur.

Preference is also given to compounds of the formula (I) in which $R^1$ is hydrogen.

Preference is also given to compounds of the formula (I) in which $R^1$ is SH.

The radical definitions specified above can be combined with one another as desired. In addition, individual definitions may not apply.

In the definitions of the symbols given in the above formulae, collective terms were used which are generally representative of the following substituents:

halogen: (also in combinations such as haloalkyl, haloalkoxy etc.) fluorine, chlorine, bromine and iodine;

alkyl: (including in combinations such as alkylthio, alkoxy etc.) saturated, straight-chain or branched hydrocarbyl radicals having 1 to 8 carbon atoms, for example $C_1$-$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl; heptyl, octyl.

Haloalkyl: (including in combinations such as haloalkylthio, haloalkoxy etc.) straight-chain or branched alkyl groups having 1 to 8 carbon atoms (as specified above), where some or all of the hydrogen atoms in these groups may be replaced by halogen atoms as specified above, for example $C_1$-$C_3$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2-difluoroethyl, 2,2-dichloro-2-fluoroethyl, 2,2,2-trichloroethyl, pentafluoroethyl and 1,1,1-trifluoroprop-2-yl.

Alkenyl: unsaturated, straight-chain or branched hydrocarbyl radicals having 2 to 8 carbon atoms and one double bond in any position, for example $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

Cycloalkyl: monocyclic saturated hydrocarbyl groups having 3 to 8 carbon ring members, such as cyclopropyl, cyclobutyl, cyclopentyl, cyclohexyl, cycloheptyl and cyclooctyl.

Aryl: unsubstituted or substituted, aromatic, mono-, bi- or tricyclic ring, for example phenyl, naphthyl, anthracenyl (anthryl), phenanthracenyl (phenanthryl).

Hetaryl: unsubstituted or substituted, unsaturated heterocyclic 5- to 7-membered ring containing up to 4 nitrogen atoms or alternatively 1 nitrogen atom and up to 2 further heteroatoms selected from N, O and S: for example 2-furyl, 3-furyl, 2-thienyl, 3-thienyl, 2-pyrrolyl, 3-pyrrolyl, 1-pyrrolyl, 3-pyrazolyl, 4-pyrazolyl, 5-pyrazolyl, 1-pyrazolyl, 1H-imidazol-2-yl, 1H-imidazol-4-yl, 1H-imidazol-5-yl, 1H-imidazol-1-yl, 2-oxazolyl, 4-oxazolyl, 5-oxazolyl, 2-thiazolyl, 4-thiazolyl, 5-thiazolyl, 3-isoxazolyl, 4-isoxazolyl, 5-isoxazolyl, 3-isothiazolyl, 4-isothiazolyl, 5-isothiazolyl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-3-yl, 1H-1,2,4-triazol-5-yl, 1H-1,2,4-triazol-1-yl, 4H-1,2,4-triazol-3-yl, 4H-1,2,4-triazol-4-yl, 1H-tetrazol-1-yl, 1H-tetrazol-5-yl, 2H-tetrazol-2-yl, 2H-tetrazol-5-yl, 1,2,4-oxadiazol-3-yl, 1,2,4-oxadiazol-5-yl, 1,2,4-thiadiazol-3-yl, 1,2,4-thiadiazol-5-yl, 1,3,4-oxadiazol-2-yl, 1,3,4-thiadiazol-2-yl, 1,2,3-oxadiazol-4-yl, 1,2,3-oxadiazol-5-yl, 1,2,3-thiadiazol-4-yl, 1,2,3-thiadiazol-5-yl, 1,2,5-oxadiazol-3-yl, 1,2,5-thiadiazol-3-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl, 1,2,4-triazin-6-yl.

Illustration of the Processes and Intermediates

The heterocyclic alkanol derivatives of the formula (I) can be prepared in different ways (cf. EP-A 0 409 418). First of all, the possible processes are shown schematically below. Unless indicated otherwise, the radicals specified are each as defined above.

Scheme 1: Process A

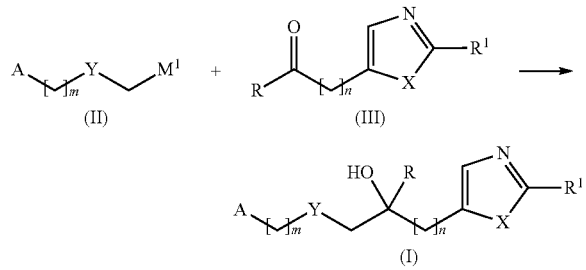

$M^1$ is a metal or metal halide, e.g. lithium, magnesium (Mg-Hal where Hal = halogen), titanium [Ti(OAlk)$_3$ where Alk = C$_1$-C$_4$-alkyl].

Scheme 2: Process B (n = 0)

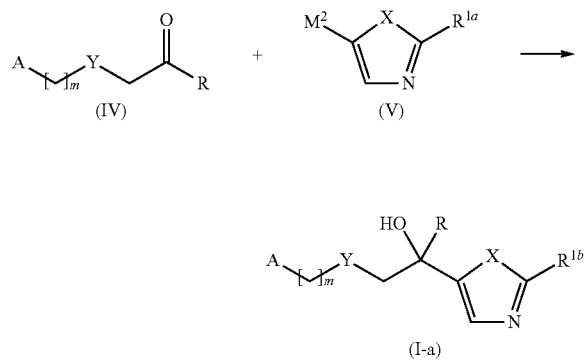

$M^2$ is a metal, e.g. lithium.
$R^{1a}$ is chlorine and Si(alkyl)$_3$.
$R^{1b}$ is hydrogen, chlorine and Si(alkyl)$_3$.

Scheme 3: Process C (n = 0, $R^1$ = H)

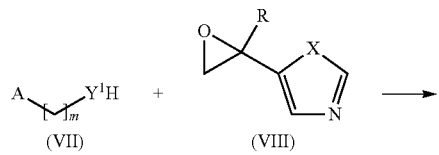

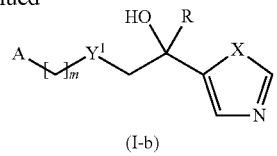

$Y^1$ is O.

Scheme 4: Process D (X = S, n = 1, $R^1$ = chlorine)

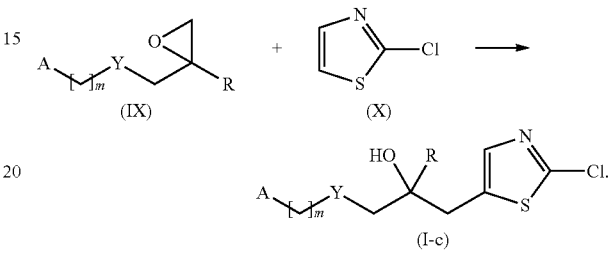

Scheme 5: Process E

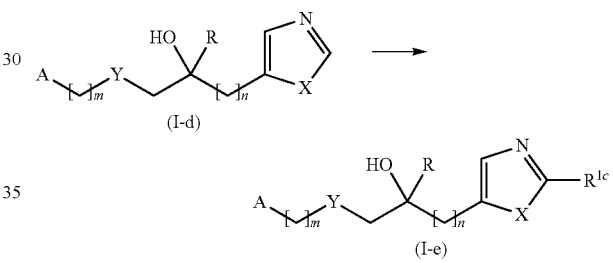

$R^{1e}$ is SH, alkylthio, alkoxy, halogen, haloalkyl, haloalkylthio, haloalkoxy, cyano, nitro.

Scheme 1: Process F

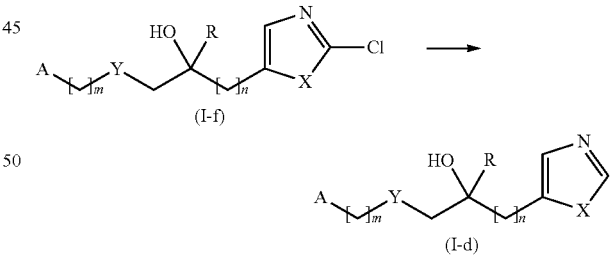

Preferred radical definitions for the formulae and schemes above and below have already been given above. These definitions apply not only to the end products of the formula (I) but likewise to all intermediates.

Process A

Some of the compounds of the formula (II) required as starting materials in the performance of process A according to the invention are known. They can be prepared in a known manner (cf. Z. Anorg. Allg. Chem. 2001, 627, 2408-2412).

The ketones of the formula (III) also required as starting materials for process A according to the invention are known (cf. EP-A 0 409 418).

Process A according to the invention is typically performed in the presence of a diluent, e.g. diethyl ether, tetrahydrofuran or dichloromethane, at temperatures of −80° C. to +80° C. The resulting product is scavenged with a proton donor.

The inventive reaction is preferably performed under inert gas such as especially nitrogen or argon.

Process B

Some of the ketones of the formula (IV) required as starting materials in the performance of process B according to the invention are known. They can be prepared in a known manner (cf. EP-A 0 409 418).

The organometallic heterocycles of the formula (V) also required as starting materials for process B according to the invention are known (cf. EP-A 0 409 418 and EP-A 0 395 175).

In the case of preparation of organometallic heterocycles of the formula (V), it may be advantageous to provide the 2 position with a suitable protecting group, e.g. trimethylsilyl, in order to direct $M^2$ into the 5 position. This protecting group can, but need not, be detached before the reaction with the ketones of the formula (IV).

Process B according to the invention is typically performed in the presence of a diluent, e.g. tetrahydrofuran or diethyl ether, at temperatures of −120° C. to +80° C. The resulting product is scavenged with a proton donor.

The inventive reaction is preferably performed under inert gas such as especially nitrogen or argon.

Process C

The compounds of the formula (VII) required as starting materials in the performance of process C according to the invention are known.

Some of the oxirane derivatives of the formula (VIII) also required as starting materials of process C according to the invention are known.

Novel oxirane derivatives are those of the formula (VIII-a)

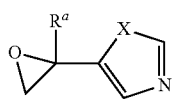

(VIII-a)

in which

X is as defined above, $R^a$ is in each case optionally substituted alkyl (excluding tert-butyl when X is S), alkenyl, cycloalkyl or aryl.

$R^a$ is preferably in each case optionally branched $C_3$-$C_7$-alkyl (excluding tert-butyl when X is S), $C_1$-$C_8$-haloalkyl, $C_2$-$C_7$-alkenyl, $C_2$-$C_7$-haloalkenyl, optionally halogen-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-haloalkylthio- or $C_1$-$C_4$-alkylthio-substituted $C_3$-$C_7$-cycloalkyl, and optionally mono- to tri-halogen- or —$C_1$-$C_4$-alkyl-substituted phenyl.

$R^a$ is more preferably in each case optionally branched $C_3$-$C_5$-alkyl excluding tert-butyl, $C_1$-$C_6$-haloalkyl, $C_3$-$C_5$-alkenyl, $C_3$-$C_5$-haloalkenyl, optionally halogen-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-haloalkylthio- or $C_1$-$C_4$-alkylthio-substituted $C_3$-$C_6$-cycloalkyl.

$R^a$ is most preferably isopropyl, 1-chlorocyclopropyl, 1-fluorocyclopropyl, 1-methylcyclopropyl, 1-methoxycyclopropyl, 1-methylthiocyclopropyl, (3E)-4-chloro-2-methylbut-3-en-2-yl, $C_1$-$C_4$-haloalkyl.

Novel oxirane derivatives of the formula (VIII-a) likewise form part of the subject-matter of this invention. Process C according to the invention is performed in the presence of a diluent, for example N,N-dimethylformamide, and optionally in the presence of a base, for example sodium hydride or potassium carbonate.

Process D

Some of the oxirane derivatives of the formula (IX) required as starting materials in the performance of process D according to the invention are known (cf. EP-A 0 121 171).

2-Chloro-1,3-thiazole (X) is known.

For conversion of IX, it is possible to use organometallic compounds, especially alkyllithium compounds (e.g. n-butyllithium) (cf. EP-A 0 395 175).

Process D according to the invention is typically performed in the presence of a diluent, for example tetrahydrofuran or diethyl ether, at temperatures of −120° C. to +80° C. The resulting product is scavenged with a proton donor. The inventive reaction is preferably performed under inert gas such as especially nitrogen or argon.

Process E

The compounds of the formula (I-d) preparable in the abovementioned processes can be converted further to the target compounds of the general structure (I-e).

For conversion of compounds of the formula (I-d), it is possible to use organometallic compounds, especially alkyllithium compounds (e.g. n-butyllithium) (cf. EP-A 0 906 292).

The organometallic compound which forms as an intermediate is typically reacted with an electrophile (e.g. sulphur, alkyl halide, interhalogen compound) to give the target compound (I-e).

Process E according to the invention is typically performed in the presence of a diluent, for example tetrahydrofuran or diethyl ether, at temperatures of −120° C. to +80° C. The resulting product is scavenged with a proton donor. The inventive reaction is preferably performed under inert gas such as especially nitrogen or argon.

Process F

The compounds of the formula (I-f) preparable in the abovementioned processes can be converted further to the target compounds of the general structure (I-d).

For conversion of compounds of the formula (I-f), it is possible to use metals, preferably zinc (cf. EP-A 0 395 175).

Process F according to the invention is typically performed in the presence of a diluent, for example tetrahydrofuran or else organic acids, for example acetic acid, at temperatures of −120° C. to +150° C.

The inventive heterocyclic alkanol derivatives of the general formula (I) can be converted to acid addition salts or metal salt complexes.

For preparation of physiologically acceptable acid addition salts of the compounds of the general formula (I), the following acids are preferred options: hydrohalic acids, for example hydrochloric acid and hydrobromic acid, especially hydrochloric acid, and also phosphoric acid, nitric acid, sulphuric acid, mono- and bifunctional carboxylic acids and hydroxycarboxylic acids, for example acetic acid, maleic acid, succinic acid, fumaric acid, tartaric acid, citric acid, salicylic acid, sorbic acid, lactic acid, and sulphonic acids, for example p-toluenesulphonic acid and 1,5-naphthalenedisulphonic acid.

The acid addition salts of the compounds of the general formula (I) can be obtained in a simple manner by customary methods for forming salts, for example by dissolving a compound of the general formula (I) in a suitable inert solvent and adding the acid, for example hydrochloric acid, and can be isolated in a known manner, for example by filtering them off, and can optionally be purified by washing with an inert organic solvent.

For preparation of metal salt complexes of the compounds of the general formula (I), preferred options are salts of metals of main group II to IV and of transition groups I and II and IV to VIII of the Periodic Table, examples of which include copper, zinc, manganese, magnesium, tin, iron and nickel.

Useful anions of the salts include those which are preferably derived from the following acids: hydrohalic acids, for example hydrochloric acid and hydrobromic acid, and also phosphoric acid, nitric acid and sulphuric acid.

The metal salt complexes of compounds of the general formula (I) can be obtained in a simple manner by customary processes, for example by dissolving the metal salt in alcohol, for example ethanol, and adding the solution to the compound of the general formula I. Metal salt complexes can be isolated in a known manner, for example by filtering them off, and can optionally be purified by recrystallization.

The present invention further relates to a crop protection composition for controlling unwanted microorganisms, especially unwanted fungi, comprising the inventive active ingredients. These are preferably fungicidal compositions which comprise agriculturally suitable auxiliaries, solvents, carriers, surfactants or extenders.

The invention also relates to a method for controlling unwanted microorganisms, characterized in that the inventive active ingredients are applied to the phytopathogenic fungi and/or their habitat.

According to the invention, a carrier is a natural or synthetic, organic or inorganic substance with which the active ingredients are mixed or combined for better applicability, in particular for application to plants or plant parts or seed. The carrier, which may be solid or liquid, is generally inert and should be suitable for use in agriculture.

Useful solid or liquid carriers include: for example ammonium salts and natural rock dusts, such as kaolins, clays, talc, chalk, quartz, attapulgite, montmorillonite or diatomaceous earth, and synthetic rock dusts, such as finely divided silica, alumina and natural or synthetic silicates, resins, waxes, solid fertilizers, water, alcohols, especially butanol, organic solvents, mineral and vegetable oils, and derivatives thereof. Mixtures of such carriers can likewise be used. Useful solid carriers for granules include: for example crushed and fractionated natural rocks such as calcite, marble, pumice, sepiolite, dolomite, and synthetic granules of inorganic and organic meals, and also granules of organic material such as sawdust, coconut shells, maize cobs and tobacco stalks.

Useful liquefied gaseous extenders or carriers are those liquids which are gaseous at standard temperature and under standard pressure, for example aerosol propellants such as halohydrocarbons, and also butane, propane, nitrogen and carbon dioxide.

In the formulations, it is possible to use tackifiers such as carboxymethylcellulose, and natural and synthetic polymers in the form of powders, granules or latices, such as gum arabic, polyvinyl alcohol and polyvinyl acetate, or else natural phospholipids such as cephalins and lecithins and synthetic phospholipids. Further additives may be mineral and vegetable oils.

If the extender used is water, it is also possible to use, for example, organic solvents as auxiliary solvents. Useful liquid solvents are essentially: aromatics such as xylene, toluene or alkylnaphthalenes, chlorinated aromatics and chlorinated aliphatic hydrocarbons such as chlorobenzenes, chloroethylenes or dichloromethane, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

The inventive compositions may additionally comprise further components, for example surfactants. Useful surfactants are emulsifiers and/or foam formers, dispersants or wetting agents having ionic or nonionic properties, or mixtures of these surfactants. Examples of these are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkylsulphates, arylsulphonates, protein hydrolysates, lignosulphite waste liquors and methylcellulose. The presence of a surfactant is necessary if one of the active ingredients and/or one of the inert carriers is insoluble in water and when application is effected in water. The proportion of surfactants is between 5 and 40 percent by weight of the inventive composition.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

If appropriate, it is also possible for other additional components to be present, for example protective colloids, binders, adhesives, thickeners, thixotropic substances, penetrants, stabilizers, sequestrants, complexing agents. In general, the active ingredients can be combined with any solid or liquid additive commonly used for formulation purposes.

The inventive compositions and formulations generally contain between 0.05 and 99% by weight, 0.01 and 98% by weight, preferably between 0.1 and 95% by weight, more preferably between 0.5 and 90% of active ingredient, most preferably between 10 and 70% by weight.

The inventive active ingredients or compositions can be used as such or, depending on their particular physical and/or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, foams, pastes, pesticide coated seed, suspension concentrates, suspoemulsion concentrates, soluble concentrates, suspensions, wettable powders, soluble powders, dusts and granules, water-soluble granules or tablets, water-soluble powders for the treatment of seed, wettable powders, natural products and synthetic substances impregnated with active ingredient, and also microencapsulations in polymeric substances and in coating materials for seed, and also ULV cold-fogging and warm-fogging formulations.

The formulations mentioned can be prepared in a manner known per se, for example by mixing the active ingredients with at least one customary extender, solvent or diluent, emulsifier, dispersant, and/or binder or fixative, wetting agent, water repellent, if appropriate desiccants and UV stabilizers and, if appropriate, dyes and pigments, antifoams, preservatives, secondary thickeners, adhesives, gibberellins and also further processing auxiliaries.

The inventive compositions include not only formulations which are already ready for use and can be applied with a suitable apparatus to the plant or the seed, but also commercial concentrates which have to be diluted with water prior to use.

The inventive active ingredients may be present as such or in their (commercial) formulations and in the use forms prepared from these formulations as a mixture with other (known) active ingredients, such as insecticides, attractants, sterilants, bactericides, acaricides, nematicides, fungicides, growth regulators, herbicides, fertilizers, safeners and/or semiochemicals.

The inventive treatment of the plants and plant parts with the active ingredients or compositions is effected directly or by action on their surroundings, habitat or storage space by the customary treatment methods, for example by dipping, spraying, atomizing, irrigating, evaporating, dusting, fogging, broadcasting, foaming, painting, spreading-on, watering (drenching), drip irrigating and, in the case of propagation material, especially in the case of seeds, also by dry seed treatment, wet seed treatment, slurry treatment, incrustation, coating with one or more coats, etc. It is also possible to deploy the active ingredients by the ultra-low volume method or to inject the active ingredient preparation or/the active ingredient itself into the soil.

The invention further comprises a method for treating seed.

The invention further relates to seed which has been treated by one of the methods described in the previous paragraph. The inventive seeds are employed in methods for the protection of seed from unwanted microorganisms. In these methods, seed treated with at least one inventive active ingredient is used.

The inventive active ingredients or compositions are also suitable for treating seed. A large part of the damage to crop plants caused by harmful organisms is triggered by the infection of the seed during storage or after sowing, and also during and after germination of the plant. This phase is particularly critical since the roots and shoots of the growing plant are particularly sensitive, and even minor damage may result in the death of the plant. There is therefore a great interest in protecting the seed and the germinating plant by using appropriate compositions.

The control of phytopathogenic fungi by treating the seed of plants has been known for a long time and is the subject of constant improvements. However, the treatment of seed entails a series of problems which cannot always be solved in a satisfactory manner. For instance, it is desirable to develop methods for protecting the seed and the germinating plant, which dispense with, or at least significantly reduce, the additional deployment of crop protection compositions after planting or after emergence of the plants. It is also desirable to optimize the amount of the active ingredient used so as to provide the best possible protection for the seed and the germinating plant from attack by phytopathogenic fungi, but without damaging the plant itself by the active ingredient employed. In particular, methods for the treatment of seed should also take account of the intrinsic fungicidal properties of transgenic plants in order to achieve optimal protection of the seed and the germinating plant with a minimum expenditure of crop protection compositions.

The present invention therefore also relates to a method for protection of seed and germinating plants from attack by phytopathogenic fungi, by treating the seed with an inventive composition. The invention likewise relates to the use of the inventive compositions for treatment of seed to protect the seed and the germinating plant from phytopathogenic fungi.

The invention further relates to seed which has been treated with an inventive composition for protection from phytopathogenic fungi.

The control of phytopathogenic fungi which damage plants post-emergence is effected primarily by treating the soil and the above-ground parts of plants with crop protection compositions. Owing to the concerns regarding a possible influence of the crop protection compositions on the environment and the health of humans and animals, there are efforts to reduce the amount of active ingredients deployed.

One of the advantages of the present invention is that the particular systemic properties of the inventive active ingredients and compositions mean that treatment of the seed with these active ingredients and compositions not only protects the seed itself, but also the resulting plants after emergence, from phytopathogenic fungi. In this way, the immediate treatment of the crop at the time of sowing or shortly thereafter can be dispensed with.

It is likewise considered to be advantageous that the inventive active ingredients or compositions can especially also be used with transgenic seed, in which case the plant growing from this seed is capable of expressing a protein which acts against pests. By virtue of the treatment of such seed with the inventive active ingredients or compositions, merely the expression of the protein, for example an insecticidal protein, can control certain pests. Surprisingly, a further synergistic effect can be observed in this case, which additionally increases the effectiveness for protection against attack by pests.

The inventive compositions are suitable for protecting seed of any plant variety which is used in agriculture, in greenhouses, in forests or in horticulture and viticulture. In particular, this is the seed of cereals (such as wheat, barley, rye, triticale, sorghum/millet and oats), maize, cotton, soya beans, rice, potatoes, sunflower, bean, coffee, beet (for example sugar beet and fodder beet), peanut, oilseed rape, poppy, olive, coconut, cocoa, sugar cane, tobacco, vegetables (such as tomato, cucumbers, onions and lettuce), turf and ornamentals (see also below). The treatment of the seed of cereals (such as wheat, barley, rye, triticale and oats), maize and rice is of particular significance.

As also described below, the treatment of transgenic seed with the inventive active ingredients or compositions is of particular significance. This relates to the seed of plants containing at least one heterologous gene which enables the expression of a polypeptide or protein having insecticidal properties. The heterologous gene in transgenic seed can originate, for example, from microorganisms of the species *Bacillus, Rhizobium, Pseudomonas, Serratia, Trichoderma, Clavibacter, Glomus* or *Gliocladium*. This heterologous gene preferably originates from *Bacillus* sp., in which case the gene product is effective against the European maize borer and/or the Western maize rootworm. The heterologous gene more preferably originates from *Bacillus thuringiensis*.

In the context of the present invention, the inventive composition is applied to the seed alone or in a suitable formulation. Preferably, the seed is treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content of less than 15% by weight. Alternatively, it is also possible to use seed which, after drying, for example, has been treated with water and then dried again.

When treating the seed, care must generally be taken that the amount of the inventive composition applied to the seed and/or the amount of further additives is selected such that the germination of the seed is not impaired, or that the resulting plant is not damaged. This has to be borne in mind in particular in the case of active ingredients which can have phytotoxic effects at certain application rates.

The inventive compositions can be applied directly, i.e. without containing any other components and without having been diluted. In general, it is preferable to apply the compositions to the seed in the form of a suitable formulation. Suitable formulations and methods for seed treatment are known to those skilled in the art and are described, for example, in the following documents: U.S. Pat. No. 4,272, 417, U.S. Pat. No. 4,245,432, U.S. Pat. No. 4,808,430, U.S. Pat. No. 5,876,739, US 2003/0176428 A1, WO 2002/080675, WO 2002/028186.

The active ingredients usable in accordance with the invention can be converted to the customary seed dressing formulations, such as solutions, emulsions, suspensions, powders, foams, slurries or other coating compositions for seed, and also ULV formulations.

These formulations are prepared in a known manner, by mixing the active ingredients with customary additives, for example customary extenders and also solvents or diluents, dyes, wetting agents, dispersants, emulsifiers, antifoams, preservatives, secondary thickeners, adhesives, gibberellins and also water.

Useful dyes which may be present in the seed dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are conventionally used for the formulation of active agrochemical ingredients. Preference is given to using alkyl naphthalenesulphonates, such as diisopropyl or diisobutyl naphthalenesulphonates.

Useful dispersants and/or emulsifiers which may be present in the seed dressing formulations usable in accordance with the invention are all nonionic, anionic and cationic dispersants conventionally used for the formulation of active agrochemical ingredients. Usable with preference are nonionic or anionic dispersants or mixtures of nonionic or anionic dispersants. Suitable nonionic dispersants include especially ethylene oxide/propylene oxide block polymers, alkylphenol polyglycol ethers and tristryrylphenol polyglycol ether, and the phosphated or sulphated derivatives thereof. Suitable anionic dispersants are especially lignosulphonates, polyacrylic acid salts and arylsulphonate/formaldehyde condensates.

Antifoams which may be present in the seed dressing formulations usable in accordance with the invention are all foam-inhibiting substances conventionally used for the formulation of active agrochemical ingredients. Silicone antifoams and magnesium stearate can be used with preference.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances usable for such purposes in agrochemical compositions. Preferred examples include cellulose derivatives, acrylic acid derivatives, xanthan, modified clays and finely divided silica.

Adhesives which may be present in the seed dressing formulations usable in accordance with the invention are all customary binders usable in seed dressing products. Preferred examples include polyvinylpyrrolidone, polyvinyl acetate, polyvinyl alcohol and tylose.

The gibberellins which may be present in the seed dressing formulations usable in accordance with the invention may preferably be gibberellins A1, A3 (=gibberellic acid), A4 and A7; particular preference is given to using gibberellic acid. The gibberellins are known (cf. R. Wegler "Chemie der Pflanzenschutz- and Schädlingsbekämp-fungsmittel" [Chemistry of the Crop Protection Compositions and Pesticides], vol. 2, Springer Verlag, 1970, p. 401-412).

The seed dressing formulations usable in accordance with the invention can be used, either directly or after previously having been diluted with water, for the treatment of a wide range of different seed, including the seed of transgenic plants. In this case, additional synergistic effects may also occur in interaction with the substances formed by expression.

For treatment of seed with the seed dressing formulations usable in accordance with the invention, or the preparations prepared therefrom by adding water, all mixing units usable customarily for the seed dressing are useful. Specifically, the procedure in the seed dressing is to place the seed into a mixer, to add the particular desired amount of seed dressing formulations, either as such or after prior dilution with water, and to mix everything until the formulation is distributed homogeneously on the seed. If appropriate, this is followed by a drying operation.

The inventive active ingredients or compositions have potent microbicidal activity and can be used for control of unwanted microorganisms, such as fungi and bacteria, in crop protection and in the protection of materials.

Fungicides can be used in crop protection for control of Plasmodiophoromycetes, Oomycetes, Chytridiomycetes, Zygomycetes, Ascomycetes, Basidiomycetes and Deuteromycetes.

Bactericides can be used in crop protection for control of Pseudomonadaceae, Rhizobiaceae, Enterobacteriaceae, Corynebacteriaceae and Streptomycetaceae.

The inventive fungicidal compositions can be used for curative or protective control of phytopathogenic fungi. The invention therefore also relates to curative and protective methods for controlling phytopathogenic fungi by the use of the inventive active ingredients or compositions, which are applied to the seed, the plant or plant parts, the fruit or the soil in which the plants grow.

The inventive compositions for controlling phytopathogenic fungi in crop protection comprise an effective but non-phytotoxic amount of the inventive active ingredients. An "effective but non-phytotoxic amount" means an amount of the inventive composition which is sufficient to control the fungal disease of the plant in a satisfactory manner or to eradicate the fungal disease completely, and which, at the same time, does not cause any significant symptoms of phytotoxicity. In general, this application rate may vary within a relatively wide range. It depends on several factors, for example on the fungus to be controlled, the plant, the climatic conditions and the ingredients of the inventive compositions.

The fact that the active ingredients are well tolerated by plants at the concentrations required for controlling plant diseases allows the treatment of above-ground parts of plants, of propagation stock and seeds, and of the soil.

All plants and plant parts can be treated in accordance with the invention. Plants are understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant varieties which are protectable and non-protectable by plant breeders' rights. Plant parts are understood to mean all parts and organs of plants above and below the ground, such as shoot, leaf, flower and root, examples of which include leaves, needles, stalks, stems, flowers, fruit bodies, fruits, seeds, roots, tubers and rhizomes. Parts of plants also include harvested material and vegetative and generative propagation material, for example seedlings, tubers, rhizomes, cuttings and seeds.

The inventive active ingredients, when they are well tolerated by plants, have favourable homeotherm toxicity and are well tolerated by the environment, are suitable for protecting plants and plant organs, for enhancing harvest yields, for improving the quality of the harvested material. They can preferably be used as crop protection compositions. They are active against normally sensitive and resistant species and against all or some stages of development.

Plants which can be treated in accordance with the invention include the following: cotton, flax, grapevine, fruit, vegetables, such as Rosaceae sp. (for example pome fruits such as apples and pears, but also stone fruits such as apricots, cherries, almonds and peaches, and soft fruits such as strawberries), Ribesioidae sp., Juglandaceae sp., Betulaceae sp., Anacardiaceae sp., Fagaceae sp., Moraceae sp., Oleaceae sp., Actimidaceae sp., Lauraceae sp., Musaceae sp. (for example banana plants and banana plantations), Rubiaceae sp. (for example coffee), Theaceae sp., Sterculiceae sp., Rutaceae sp. (for example lemons, oranges and grapefruit); Solanaceae sp. (for example tomatoes), Liliaceae sp., Asteraceae sp. (for example lettuce), Umbelliferae sp., Cruciferae sp., Chenopodiaceae sp., Cucurbitaceae sp. (for example cucumber), Alliaceae sp. (for example leeks, onions), Papilionaceae sp. (for example peas); major crop plants such as Gramineae sp. (for example maize, turf, cereals such as wheat, rye, rice, barley, oats, millet and triticale), Poaceae sp. (for example sugar cane), Asteraceae sp. (for example sunflower), Brassicaceae sp. (for example white cabbage, red cabbage, broccoli, cauliflower, Brussels sprouts, pak Choi, kohlrabi, radishes, and also oilseed rape, mustard, horseradish and cress), Fabacae sp. (for example beans, peanuts), Papilionaceae sp. (for example soya beans), Solanaceae sp. (for example potatoes), Chenopodiaceae sp. (for example sugar beet, fodder beet, Swiss chard, beetroot); useful plants and ornamental plants in gardens and forests; and genetically modified types of each of these plants.

As already mentioned above, it is possible to treat all plants and their parts according to the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above. More preferably, plants of the plant cultivars which are each commercially available or in use are treated in accordance with the invention. Plant cultivars are understood to mean plants which have new properties ("traits") and have been obtained by conventional breeding, by mutagenesis or by recombinant DNA techniques. They can be cultivars, varieties, bio- or genotypes.

The inventive treatment method can be used for the treatment of genetically modified organisms (GMOs), for example plants or seeds. Genetically modified plants (or transgenic plants) are plants in which a heterologous gene has been integrated stably into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example antisense technology, cosuppression technology or RNAi technology [RNA interference]). A heterologous gene present in the genome is also called a transgene. A transgene that is defined by its specific presence in the plant genome is called a transformation or transgenic event.

Depending on the plant species or plant varieties, their location and growth conditions (soils, climate, vegetation period, diet), the treatment according to the invention may also result in superadditive ("synergistic") effects. For example, the following effects exceeding the effects actually to be expected are possible: reduced application rates and/or a widening of the activity spectrum and/or an increase in the activity of the active ingredients and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf colour, earlier flowering, higher quality and/or a higher nutritional value of the harvested products, higher sugar concentration within the fruits, better storage stability and/or processibility of the harvested products.

At certain application rates, the inventive active ingredients may also have a fortifying effect on plants. They are therefore suitable for mobilizing the defence system of the plant against attack by unwanted phytopathogenic fungi and/or microorganisms and/or viruses. This may be one of the reasons for the enhanced activity of the inventive combinations, for example against fungi. Plant-fortifying (resistance-inducing) substances shall be understood to mean, in the present context, also those substances or combinations of substances which are capable of stimulating the defence system of plants in such a way that, when subsequently inoculated with unwanted phytopathogenic fungi, the plants treated display a substantial degree of resistance to these unwanted phytopathogenic fungi. The inventive substances can therefore be used for protection of plants from attack by the pathogens mentioned within a certain period of time after the treatment. The period within which protection is achieved generally extends for from 1 to 10 days, preferably 1 to 7 days, after the treatment of the plants with the active ingredients.

Plants and plant varieties which are preferably treated in accordance with the invention include all plants which have genetic material which imparts particularly advantageous, useful traits to these plants (whether obtained by breeding and/or biotechnological means).

Plants and plant varieties which are likewise preferably treated in accordance with the invention are resistant to one or more biotic stress factors, i.e. said plants have a better defence against animal and microbial pests, such as against nematodes, insects, mites, phytopathogenic fungi, bacteria, viruses and/or viroids.

Plants and plant varieties which may also be treated according to the invention are those plants which are resistant to one or more abiotic stress factors. Abiotic stress conditions may include, for example, drought, cold temperature exposure, heat exposure, osmotic stress, waterlogging, increased soil salinity, increased exposure to minerals, exposure to ozone, exposure to strong light, limited availability of nitrogen nutrients, limited availability of phosphorus nutrients or shade avoidance.

Plants and plant varieties which can likewise be treated in accordance with the invention are those plants which are characterized by enhanced yield characteristics. Enhanced yield in these plants may be the result of, for example, improved plant physiology, improved plant growth and development, such as water use efficiency, water retention efficiency, improved nitrogen use, enhanced carbon assimilation, improved photosynthesis, increased germination efficiency and accelerated maturation. Yield can also be affected by improved plant architecture (under stress and non-stress conditions), including early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processibility and better storage stability.

Plants that may be treated according to the invention are hybrid plants that already express the characteristics of heterosis, or hybrid effect, which results in generally higher yield, vigour, health and resistance towards biotic and abiotic stress factors. Such plants are typically produced by crossing an inbred male-sterile parent line (the female parent) with another inbred male-fertile parent line (the male parent). The hybrid seed is typically harvested from the male-sterile plants and sold to growers. Male-sterile plants can sometimes (for example in maize) be produced by detasseling (i.e. mechanical removal of the male reproductive organs or male flowers); however, it is more typical for male sterility to be the result of genetic determinants in the plant genome. In that case, and especially when seed is the desired product to be harvested from the hybrid plants, it is typically beneficial to ensure that male fertility in hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for *Brassica* species. However, genetic determinants for male sterility can also be located in the nuclear genome. Male-sterile plants can also be obtained by plant biotechnology methods such as genetic engineering. A particularly useful means of obtaining male-sterile plants is described in WO 89/10396, in which, for example, a ribonuclease such as a barnase is selectively expressed in the tapetum cells in the stamens. Fertility can then be restored by expression in the tapetum cells of a ribonuclease inhibitor such as barstar.

Plants or plant varieties (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are, for example, glyphosate-tolerant plants, i.e. plants which have been made tolerant to the herbicide glyphosate or salts thereof. For example, glyphosate-tolerant plants can be obtained by transforming the plant with a gene which encodes the enzyme 5-enolpyruvylshikimate-3-phosphate synthase (EPSPS). Examples of such EPSPS genes are the AroA gene (mutant CT7) of the bacterium *Salmonella typhimurium*, the CP4 gene of the bacterium *Agrobacterium* sp., the genes encoding a petunia EPSPS, a tomato EPSPS, or an *Eleusine* EPSPS. It can also be a mutated EPSPS. Glyphosate-tolerant plants can also be obtained by expressing a gene that encodes a glyphosate oxidoreductase enzyme. Glyphosate-tolerant plants can also be obtained by expressing a gene that encodes a glyphosate acetyltransferase enzyme. Glyphosate-tolerant plants can also be obtained by selecting plants containing naturally occurring mutations of the abovementioned genes.

Other herbicide-resistant plants are for example plants that have been made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is, for example, an enzyme encoding a phosphinothricin acetyltransferase (such as the bar or pat protein from *Streptomyces* species). Plants expressing an exogenous phosphinothricin acetyltransferase have been described.

Further herbicide-tolerant plants are also plants that have been made tolerant to the herbicides inhibiting the enzyme hydroxyphenylpyruvatedioxygenase (HPPD). Hydroxyphenylpyruvatedioxygenases are enzymes that catalyse the reaction in which para-hydroxyphenylpyruvate (HPP) is converted to homogentisate. Plants tolerant to HPPD inhibitors can be transformed with a gene encoding a naturally occurring resistant HPPD enzyme, or a gene encoding a mutated HPPD enzyme. Tolerance to HPPD inhibitors can also be obtained by transforming plants with genes encoding certain enzymes enabling the formation of homogentisate despite the inhibition of the native HPPD enzyme by the HPPD inhibitor. Tolerance of plants to HPPD inhibitors can also be improved by transforming plants with a gene encoding an enzyme prephenate dehydrogenase in addition to a gene encoding an HPPD-tolerant enzyme.

Further herbicide-resistant plants are plants that have been made tolerant to acetolactate synthase (ALS) inhibitors. The known ALS inhibitors include, for example, sulphonylurea, imidazolinone, triazolopyrimidines, pyrimidinyl oxy(thio)benzoates and/or sulphonylaminocarbonyltriazolinone herbicides. Different mutations in the ALS enzyme (also known as acetohydroxy acid synthase, AHAS) are known to confer tolerance to different herbicides and groups of herbicides. The production of sulphonylurea-tolerant plants and imidazolinone-tolerant plants has been described in the international publication WO 1996/033270. Further sulphonylurea- and imidazolinone-tolerant plants have also been described, for example in WO 2007/024782.

Other plants tolerant to imidazolinone and/or sulphonylurea can be obtained by induced mutagenesis, by selection in cell cultures in the presence of the herbicide or by mutation breeding.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation which imparts such insect resistance.

In the present context, the term "insect-resistant transgenic plant" includes any plant containing at least one transgene comprising a coding sequence encoding:

1) an insecticidal crystal protein from *Bacillus thuringiensis* or an insecticidal portion thereof, for example proteins of the Cry protein classes Cry1Ab, Cry1Ac, Cry1F, Cry2Ab, Cry3Ae or Cry3Bb or insecticidal portions thereof; or 2) a crystal protein from *Bacillus thuringiensis* or a portion thereof which is insecticidal in the presence of a second other crystal protein than *Bacillus thuringiensis* or a portion thereof, such as the binary toxin made up of the Cy34 and Cy35 crystal proteins; or 3) a hybrid insecticidal protein comprising parts of two different insecticidal crystal proteins from *Bacillus thuringiensis*, such as a hybrid of the proteins of 1) above or a hybrid of the proteins of 2) above, for example the Cry1A.105 protein produced by maize event MON98034 (WO 2007/027777); or 4) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation, such as the Cry3Bb1 protein in maize events MON863 or MON88017, or the Cry3A protein in maize event MIR604; or 5) an insecticidal secreted protein from *Bacillus thuringiensis* or *Bacillus cereus*, or an insecticidal portion thereof, such as the vegetative insecticidal proteins (VIP), for example proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins; or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or trans-formation (while still encoding an insecticidal protein), such as the VIP3Aa protein in cotton event COT102.

Of course, insect-resistant transgenic plants, as used herein, also include any plant comprising a combination of genes encoding the proteins of any one of the abovementioned classes 1 to 8. In one embodiment, an insect-resistant plant contains more than one transgene encoding a protein of any one of the abovementioned classes 1 to 8, to expand the range of target insect species affected or to delay insect resistance development to the plants, by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stress factors. Such plants can be obtained by genetic transformation, or by selection of plants containing a mutation imparting such stress resistance. Particularly useful stress-tolerant plants include the following:

a. plants which contain a transgene capable of reducing the expression and/or the activity of the poly(ADP-ribose) polymerase (PARP) gene in the plant cells or plants;

b. plants which contain a stress tolerance-enhancing transgene capable of reducing the expression and/or the activity of the PARG-encoding genes of the plants or plant cells;

c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase.

Plants or plant cultivars (obtained by plant biotechnology methods such as genetic engineering) which may also be treated according to the invention show altered quantity, quality and/or storage stability of the harvested product and/or altered properties of specific ingredients of the harvested product such as:

1) Transgenic plants which synthesize a modified starch which is altered with respect to its chemophysical traits, in particular the amylose content or the amylose/amylopectin ratio, the degree of branching, the average chain length, the distribution of the side chains, the viscosity behaviour, the gel resistance, the grain size and/or grain morphology of the starch in comparison to the synthesized starch in wild-type plant cells or plants, such that this modified starch is better suited for certain applications.

2) Transgenic plants which synthesize non-starch carbohydrate polymers or which synthesize non-starch carbohydrate polymers with altered properties in comparison to wild-type plants without genetic modification. Examples are plants which produce polyfructose, especially of the inulin and levan type, plants which produce alpha-1,4-glucans, plants which produce alpha-1,6-branched alpha-1,4-glucans, and plants producing alternan.

3) Transgenic plants which produce hyaluronan.

Plants or plant cultivars (obtained by plant biotechnology methods such as genetic engineering) which may also be treated according to the invention are plants, such as cotton plants, with altered fibre characteristics. Such plants can be obtained by genetic transformation, or by selection of plants containing a mutation imparting such altered fibre characteristics and include:

a) plants, such as cotton plants, which contain an altered form of cellulose synthase genes;

b) plants, such as cotton plants, which contain an altered form of rsw2 or rsw3 homologous nucleic acids;

c) plants, such as cotton plants, with an increased expression of sucrose phosphate synthase;

d) plants, such as cotton plants, with an increased expression of sucrose synthase;

e) plants, such as cotton plants, wherein the timing of the plasmodesmatal gating at the basis of the fibre cell is altered, for example through downregulation of fibre-selective β-1,3-glucanase;

f) plants, such as cotton plants, which have fibres with altered reactivity, for example through the expression of the N-acetylglucosaminetransferase gene including nodC and chitin synthase genes.

Plants or plant cultivars (obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants containing a mutation imparting such altered oil characteristics and include:
a) plants, such as oilseed rape plants, which produce oil having a high oleic acid content;
b) plants, such as oilseed rape plants, which produce oil having a low linolenic acid content;
c) plants, such as oilseed rape plants, which produce oil having a low level of saturated fatty acids.

Particularly useful transgenic plants which may be treated according to the invention are plants which comprise one or more genes which encode one or more toxins are the transgenic plants which are sold under the following trade names: YIELD GARD® (for example maize, cotton, soya beans), KnockOut® (for example maize), BiteGard® (for example maize), BT-Xtra® (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which should be mentioned are maize varieties, cotton varieties and soya bean varieties which are available under the following trade names: Roundup Ready® (tolerance to glyphosate, for example maize, cotton, soya beans), Liberty Link® (tolerance to phosphinothricin, for example oilseed rape), IMI® (tolerance to imidazolinone) and SCS® (tolerance to sulphonylurea, for example maize). Herbicide-resistant plants (plants bred in a conventional manner for herbicide tolerance) which should be mentioned include the varieties sold under the Clearfield® name (for example maize).

Particularly useful transgenic plants which may be treated according to the invention are plants containing trans-formation events, or a combination of transformation events, and that are listed for example in the databases for various national or regional regulatory agencies.

The inventive active ingredients or compositions can also be used in the protection of materials, for protection of industrial materials against attack and destruction by unwanted microorganisms, for example fungi and insects.

In addition, the inventive compounds can be used as antifouling compositions, alone or in combinations with other active ingredients.

Industrial materials in the present context are understood to mean inanimate materials which have been prepared for use in industry. For example, industrial materials which are to be protected by inventive active ingredients from microbial alteration or destruction may be adhesives, sizes, paper, wallpaper and board, textiles, carpets, leather, wood, paints and plastic articles, cooling lubricants and other materials which can be infected with or destroyed by microorganisms. Parts of production plants and buildings, for example cooling-water circuits, cooling and heating systems and ventilation and air-conditioning units, which may be impaired by the proliferation of microorganisms may also be mentioned within the scope of the materials to be protected. Industrial materials within the scope of the present invention preferably include adhesives, sizes, paper and card, leather, wood, paints, cooling lubricants and heat transfer fluids, more preferably wood. The inventive active ingredients or compositions may prevent adverse effects, such as rotting, decay, discoloration, decoloration or formation of mould. In addition, the inventive compounds can be used to protect objects which come into contact with saltwater or brackish water, especially hulls, screens, nets, buildings, moorings and signalling systems, from fouling.

The inventive method for controlling unwanted fungi can also be employed for protecting storage goods. Storage goods are understood to mean natural substances of vegetable or animal origin or processed products thereof which are of natural origin, and for which long-term protection is desired. Storage goods of vegetable origin, for example plants or plant parts, such as stems, leaves, tubers, seeds, fruits, grains, can be protected freshly harvested or after processing by (pre) drying, moistening, comminuting, grinding, pressing or roasting. Storage goods also include timber, both unprocessed, such as construction timber, electricity poles and barriers, or in the form of finished products, such as furniture. Storage goods of animal origin are, for example, hides, leather, furs and hairs. The inventive active ingredients may prevent adverse effects, such as rotting, decay, discoloration, decoloration or formation of mould.

Non-limiting examples of pathogens of fungal diseases which can be treated in accordance with the invention include:
diseases caused by powdery mildew pathogens, for example *Blumeria* species, for example *Blumeria graminis*; *Podosphaera* species, for example *Podosphaera leucotricha*; *Sphaerotheca* species, for example *Sphaerotheca fuliginea*; *Uncinula* species, for example *Uncinula necator*;
diseases caused by rust disease pathogens, for example *Gymnosporangium* species, for example *Gymnosporangium sabinae*; *Hemileia* species, for example *Hemileia vastatrix*; *Phakopsora* species, for example. *Phakopsora pachyrhizi* and *Phakopsora meibomiae*; *Puccinia* species, for example *Puccinia recondita* or *Puccinia triticina*; *Uromyces* species, for example *Uromyces appendiculatus*;
diseases caused by pathogens from the group of the Oomycetes, for example *Bremia* species, for example *Bremia lactucae*; *Peronospora* species, for example *Peronospora pisi* or *P. brassicae*; *Phytophthora* species, for example *Phytophthora infestans*; *Plasmopara* species, for example *Plasmopara viticola*; *Pseudoperonospora* species, for example *Pseudoperonospora humuli* or *Pseudoperonospora cubensis*; *Pythium* species, for example *Pythium ultimum*;
leaf blotch diseases and leaf wilt diseases caused, for example, by *Alternaria* species, for example *Alternaria solani*; *Cercospora* species, for example *Cercospora beticola*; *Cladiosporium* species, for example *Cladiosporium cucumerinum*; *Cochliobolus* species, for example *Cochliobolus sativus* (conidia form: *Drechslera*, Syn: *Helminthosporium*); *Colletotrichum* species, for example *Colletotrichum lindemuthanium*; *Cycloconium* species, for example *Cycloconium oleaginum*; *Diaporthe* species, for example *Diaporthe citri*; *Elsinoe* species, for example *Elsinoe fawcettii*; *Gloeosporium* species, for example *Gloeosporium laeticolor*; *Glomerella* species, for example *Glomerella cingulata*; *Guignardia* species, for example *Guignardia bidwelli*; *Leptosphaeria* species, for example *Leptosphaeria maculans*; *Magnaporthe* species, for example *Magnaporthe grisea*; *Microdochium* species, for example *Microdochium nivale*; *Mycosphaerella* species, for example *Mycosphaerella graminicola* and *M. fijiensis*; *Phaeosphaeria* species, for example *Phaeosphaeria nodorum*; *Pyrenophora* species, for example *Pyrenophora teres*; *Ramularia* species, for example *Ramularia collo-cygni*; *Rhynchosporium* species, for example *Rhynchosporium secalis*; *Septoria* species, for example *Septoria apii*; *Typhula* species, for example *Typhula incarnata*; *Venturia* species, for example *Venturia inaequalis*;
root and stem diseases caused, for example, by *Corticium* species, for example *Corticium graminearum*; *Fusarium* species, for example *Fusarium oxysporum*; *Gaeumannomyces* species, for example *Gaeumannomyces graminis*; *Rhizoctonia* species, for example *Rhizoctonia solani*; *Tapesia* species, for example *Tapesia acuformis*; *Thielaviopsis* species, for example *Thielaviopsis basicola*;

ear and panicle diseases (including maize cobs) caused, for example, by *Alternaria* species, for example *Alternaria* spp.; *Aspergillus* species, for example *Aspergillus flavus*; *Cladosporium* species, for example *Cladosporium cladosporioides*; *Claviceps* species, for example *Claviceps purpurea*; *Fusarium* species, for example *Fusarium culmorum*; *Gibberella* species, for example *Gibberella zeae*; *Monographella* species, for example *Monographella nivalis*; *Septoria* species, for example *Septoria nodorum*;

diseases caused by smut fungi, for example *Sphacelotheca* species, for example *Sphacelotheca reiliana*; *Tilletia* species, for example *Tilletia caries*, *T. controversa*; *Urocystis* species, for example *Urocystis occulta*; *Ustilago* species, for example *Ustilago nuda*, *U. nuda tritici*;

fruit rot caused, for example, by *Aspergillus* species, such as, for example, *Aspergillus flaws*; *Botrytis* species, such as, for example, *Botrytis cinerea*; *Penicillium* species, such as, for example, *Penicillium expansum* and *P. purpurogenum*; *Sclerotinia* species, such as, for example, *Sclerotinia sclerotiorum*;

*Verticilium* species, for example *Verticilium alboatrum*;

seed- and soil-borne rot and wilt diseases, and also diseases of seedlings, caused, for example, by *Fusarium* species, for example *Fusarium culmorum*; *Phytophthora* species, for example *Phytophthora cactorum*; *Pythium* species, for example *Pythium ultimum*; *Rhizoctonia* species, for example *Rhizoctonia solani*; *Sclerotium* species, for example *Sclerotium rolfsii*;

cancers, galls and witches' broom caused, for example, by *Nectria* species, for example *Nectria galligena*;

wilt diseases caused, for example, by *Monilinia* species, for example *Monilinia laxa*;

deformations of leaves, flowers and fruits caused, for example, by *Taphrina* species, for example *Taphrina deformans*;

degenerative diseases of woody plants caused, for example, by *Esca* species, for example *Phaeomoniella chlamydospora* and *Phaeoacremonium aleophilum* and *Fomitiporia mediterranea*;

diseases of flowers and seeds caused, for example, by *Botrytis* species, for example *Botrytis cinerea*;

diseases of plant tubers caused, for example, by *Rhizoctonia* species, for example *Rhizoctonia solani*; *Helminthosporium* species, for example *Helminthosporium solani*;

diseases caused by bacterial pathogens, for example *Xanthomonas* species, for example *Xanthomonas campestris* pv. *oryzae*; *Pseudomonas* species, for example *Pseudomonas syringae* pv. *lachrymans*; *Erwinia* species, for example *Erwinia amylovora*.

Preference is given to controlling the following diseases of soya beans:

Fungal diseases on leaves, stems, pods and seeds caused, for example, by alternaria leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi*, *Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum*, *Fusarium orthoceras*, *Fusarium semitectum*, *Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum*, *Pythium irregulare*, *Pythium debaryanum*, *Pythium myriotylum*, *Pythium ultimum*), rhizoctonia root rot, stem decay, and damping-off (*Rhizoctonia solani*), sclerotinia stem decay (*Sclerotinia sclerotionun*), sclerotinia southern blight (*Sclerotinia rolfsii*), thielaviopsis root rot (*Thielaviopsis basicola*).

Microorganisms capable of degrading or altering the industrial materials include, for example, bacteria, fungi, yeasts, algae and slime organisms. The inventive active ingredients preferably act against fungi, especially moulds, wood-discoloring and wood-destroying fungi (Basidiomycetes), and against slime organisms and algae. Examples include microorganisms of the following genera: *Alternaria*, such as *Alternaria tenuis*; *Aspergillus*, such as *Aspergillus niger*; *Chaetomium*, such as *Chaetomium globosum*; *Coniophora*, such as *Coniophora puetana*; *Lentinus*, such as *Lentinus tigrinus*; *Penicillium*, such as *Penicillium glaucum*; *Polyporus*, such as *Polyporus versicolor*; *Aureobasidium*, such as *Aureobasidium pullulans*; *Sclerophoma*, such as *Sclerophoma pityophila*; *Trichoderma*, such as *Trichoderma viride*; *Escherichia*, such as *Escherichia coli*; *Pseudomonas*, such as *Pseudomonas aeruginosa*; *Staphylococcus*, such as *Staphylococcus aureus*.

In addition, the inventive active ingredients also have very good antimycotic activity. They have a very broad antimycotic activity spectrum, especially against dermatophytes and yeasts, moulds and diphasic fungi (for example against *Candida* species, such as *Candida albicans*, *Candida glabrata*), and *Epidermophyton floccosum*, *Aspergillus* species, such as *Aspergillus niger* and *Aspergillus fumigatus*, *Trichophyton* species, such as *Trichophyton mentagrophytes*, *Microsporon* species such as *Microsporon canis* and *audouinii*. The list of these fungi by no means constitutes a restriction of the mycotic spectrum covered, and is merely of illustrative character.

The inventive active ingredients can therefore be used both in medical and in non-medical applications.

When using the inventive active ingredients as fungicides, the application rates can be varied within a relatively wide range, depending on the kind of application. The application rate of the inventive active ingredients is in the case of treatment of plant parts, for example leaves: from 0.1 to 10 000 g/ha, preferably from 10 to 1000 g/ha, more preferably from 50 to 300 g/ha (in the case of application by watering or dripping, it is even possible to reduce the application rate, especially when inert substrates such as rockwool or perlite are used);

in the case of seed treatment: from 2 to 200 g per 100 kg of seed, preferably from 3 to 150 g per 100 kg of seed, more preferably from 2.5 to 25 g per 100 kg of seed, even more preferably from 2.5 to 12.5 g per 100 kg of seed;

in the case of soil treatment: from 0.1 to 10 000 g/ha, preferably from 1 to 5000 g/ha.

These application rates are merely by way of example and are not limiting for the purposes of the invention.

The inventive active ingredients or compositions can thus be used to protect plants from attack by the pathogens mentioned for a certain period of time after treatment. The period for which protection is provided extends generally for 1 to 28 days, preferably for 1 to 14 days, more preferably for 1 to 10 days, most preferably for 1 to 7 days, after the treatment of the plants with the active ingredients, or for up to 200 days after a seed treatment.

In addition, the inventive treatment can reduce the mycotoxin content in the harvested material and the foods and feeds prepared therefrom. Mycotoxins include particularly, but not exclusively, the following: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaroproliferin, fusarenol, ochratoxins, patulin, ergot alkaloids and aflatoxins which can be produced, for example, by the following fungi: *Fusarium* spec., such as *Fusarium acuminatum, F. avenaceum, F. crookwellense, F. culmorum, F. graminearum (Gibberella zeae), F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides*, inter alia, and also by *Aspergillus* spec., *Penicillium* spec., *Claviceps purpurea, Stachybotrys* spec., inter alia.

In some cases, the inventive compounds can, at particular concentrations or application rates, also be used as herbicides, safeners, growth regulators or agents to improve plant properties, or as microbicides, for example as fungicides, antimycotics, bactericides, viricides (including compositions against viroids) or as compositions against MLO (Mycoplasma-like organisms) and RLO (Rickettsia-like organisms). If appropriate, they can also be used as intermediates or precursors for the synthesis of other active ingredients.

The inventive active ingredients intervene in the metabolism of the plants and can therefore also be used as growth regulators.

Plant growth regulators may exert various effects on plants. The effect of the substances depends essentially on the time of application in relation to the developmental stage of the plant, and also on the amounts of active ingredient applied to the plants or their environment and on the type of application. In each case, growth regulators should have a particular desired effect on the crop plants.

Plant growth-regulating compounds can be used, for example, to inhibit the vegetative growth of the plants. Such inhibition of growth is of economic interest, for example, in the case of grasses, since it is thus possible to reduce the frequency of grass cutting in ornamental gardens, parks and sport facilities, on roadsides, at airports or in fruit crops. Also of significance is the inhibition of the growth of herbaceous and woody plants on roadsides and in the vicinity of pipelines or overhead cables, or quite generally in areas where vigorous plant growth is unwanted.

Also important is the use of growth regulators for inhibition of the longitudinal growth of cereal. This reduces or completely eliminates the risk of lodging of the plants prior to harvest. In addition, growth regulators in the case of cereals can strengthen the culm, which also counteracts lodging. The employment of growth regulators for shortening and strengthening culms allows the deployment of higher fertilizer volumes to increase the yield, without any risk of lodging of the cereal crop.

In many crop plants, inhibition of vegetative growth allows denser planting, and it is thus possible to achieve higher yields based on the soil surface. Another advantage of the smaller plants obtained in this way is that the crop is easier to cultivate and harvest.

Inhibition of the vegetative plant growth may also lead to enhanced yields because the nutrients and assimilates are of more benefit to flower and fruit formation than to the vegetative parts of the plants.

Frequently, growth regulators can also be used to promote vegetative growth. This is of great benefit when harvesting the vegetative plant parts. However, promoting vegetative growth may also promote generative growth in that more assimilates are formed, resulting in more or larger fruits.

In some cases, yield increases may be achieved by manipulating the metabolism of the plant, without any detectable changes in vegetative growth. In addition, growth regulators can be used to alter the composition of the plants, which in turn may result in an improvement in quality of the harvested products. For example, it is possible to increase the sugar content in sugar beet, sugar cane, pineapples and in citrus fruit, or to increase the protein content in soya or cereals. It is also possible, for example, to use growth regulators to inhibit the degradation of desirable ingredients, for example sugar in sugar beet or sugar cane, before or after harvest. It is also possible to positively influence the production or the elimination of secondary plant ingredients. One example is the stimulation of the flow of latex in rubber trees.

Under the influence of growth regulators, parthenocarpic fruits may be formed. In addition, it is possible to influence the sex of the flowers. It is also possible to produce sterile pollen, which is of great importance in the breeding and production of hybrid seed.

Use of growth regulators can control the branching of the plants. On the one hand, by breaking apical dominance, it is possible to promote the development of side shoots, which may be highly desirable particularly in the cultivation of ornamental plants, also in combination with an inhibition of growth. On the other hand, however, it is also possible to inhibit the growth of the side shoots. This effect is of particular interest, for example, in the cultivation of tobacco or in the cultivation of tomatoes.

Under the influence of growth regulators, the amount of leaves on the plants can be controlled such that defoliation of the plants is achieved at a desired time. Such defoliation plays a major role in the mechanical harvesting of cotton, but is also of interest for facilitating harvesting in other crops, for example in viticulture. Defoliation of the plants can also be undertaken to lower the transpiration of the plants before they are transplanted.

Growth regulators can likewise be used to regulate fruit dehiscence. On the one hand, it is possible to prevent premature fruit dehiscence. On the other hand, it is also possible to promote fruit dehiscence or even flower abortion to achieve a desired mass ("thinning"), in order to eliminate alternation. Alternation is understood to mean the characteristic of some fruit species, for endogenous reasons, to deliver very different yields from year to year. Finally, it is possible to use growth regulators at the time of harvest to reduce the forces required to detach the fruits, in order to allow mechanical harvesting or to facilitate manual harvesting.

Growth regulators can also be used to achieve faster or else delayed ripening of the harvested material before or after harvest. This is particularly advantageous as it allows optimal adjustment to the requirements of the market. Moreover, growth regulators in some cases can improve the fruit colour. In addition, growth regulators can also be used to concentrate maturation within a certain period of time. This establishes the prerequisites for complete mechanical or manual harvesting in a single operation, for example in the case of tobacco, tomatoes or coffee.

By using growth regulators, it is additionally possible to influence the resting of seed or buds of the plants, such that plants such as pineapple or ornamental plants in nurseries, for example, germinate, sprout or flower at a time when they are normally not inclined to do so. In areas where there is a risk of frost, it may be desirable to delay budding or germination of seeds with the aid of growth regulators, in order to avoid damage resulting from late frosts.

Finally, growth regulators can induce resistance of the plants to frost, drought or high salinity of the soil. This allows the cultivation of plants in regions which are normally unsuitable for this purpose.

The plants listed can particularly advantageously be treated in accordance with the invention with the compounds of the general formula (I) and the inventive compositions. The preferred ranges stated above for the active ingredients or compositions also apply to the treatment of these plants. Particular emphasis is given to the treatment of plants with the compounds or compositions specifically mentioned in the present text.

The invention is illustrated by the examples below. However, the invention is not limited to the examples.

PREPARATION EXAMPLES

Preparation of Compound No. 2

Process C

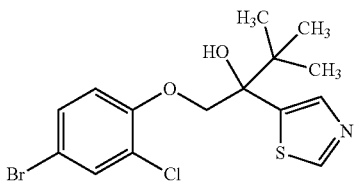 [SMILES: CC(C)(C)C(O)(COc1ccc(Br)cc1Cl)c1cncs1]

To 0.62 g (3.0 mmol) of 4-bromo-2-chlorophenol dissolved in 10 ml of N,N-dimethylformamide was added, at room temperature under an argon atmosphere, 0.12 g (60%, 3.0 mmol) of sodium hydride, and the reaction mixture was stirred at room temperature for 1 h. Then 0.50 g (2.7 mmol) of 5-(2-tert-butyloxiran-2-yl)-1,3-thiazole was added and the reaction mixture was stirred at 100° C. for 12 h. After cooling to room temperature, the solvent was removed under reduced pressure, and saturated aqueous sodium chloride solution and ethyl acetate were added to the residue. The organic phase was removed, dried over sodium sulphate, filtered and concentrated. The crude product was then purified by column chromatography (3:1 cyclohexane/ethyl acetate). This gave 0.24 g (23%) of the desired product.

Preparation of
5-(2-tert-butyloxiran-2-yl)-1,3-thiazole

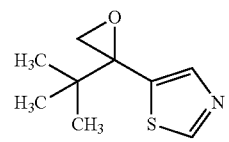

The preparation is effected analogously to the process described in EP-A 0 409 418.

Preparation of Compound No. 31

Process A

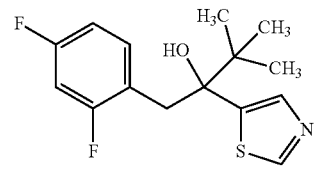 [SMILES: CC(C)(C)C(O)(Cc1ccc(F)cc1F)c1cncs1]

To 0.30 g (1.8 mmol) of 2,2-dimethyl-1-(1,3-thiazol-5-yl)propan-1-one dissolved in 10 ml of diethyl ether were added, at −10° C. under an argon atmosphere, 21 ml (0.25 M in diethyl ether, 5.3 mmol) of 2,4-difluorobenzylmagnesium bromide, and the reaction mixture was warmed to room temperature. The reaction mixture was then stirred at room temperature for 12 h. After addition of saturated aqueous ammonium chloride solution, the phases were separated and the aqueous phase was extracted with ethyl acetate. The combined organic phases were dried over sodium sulphate, filtered and concentrated. The crude product was then purified by column chromatography (5:1 cyclohexane/ethyl acetate). This gave 0.20 g (39%) of the desired product

TABLE 1

(I)

| No. | X | Y | m | n | R | R$^1$ | A | Physical data |
|---|---|---|---|---|---|---|---|---|
| 1 | S | O | 0 | 0 | tBu | H | 2-fluoro-4-iodophenyl | $^1$H NMR: δ (400 MHz, DMSO-d6) = 0.98 (s, 9H), 4.25 (d, J = 10 Hz, 1H), 4.40 (d, J = 10 Hz, 1H), 5.75 (s, 1H), 7.07 (m, 1H), 7.47 (m, 1H), 7.57 (m, 1H), 7.76 (s, 1H), 8.93 (s, 1H) ppm. |

TABLE 1-continued (I)

| No. | X | Y | m | n | R | R¹ | A | Physical data |
|---|---|---|---|---|---|---|---|---|
| 2 | S | O | 0 | 0 | tBu | H | 4-bromo-2-chlorophenyl | ¹H NMR: δ (400 MHz, DMSO-d6) = 0.97 (s, 9H), 4.25 (d, J = 10 Hz, 1H), 4.38 (d, J = 10 Hz, 1H), 5.69 (s, 1H), 7.17 (d, J = 9 Hz, 1H), 7.48 (dd, J = 9 Hz, 2 Hz, 1H), 7.63 (d, J = 2 Hz, 1H), 7.81 (s, 1H), 8.92 (s, 1H) ppm. |
| 3 | S | O | 0 | 0 | tBu | H | 4-bromo-2-fluorophenyl | ¹H NMR: δ (400 MHz, DMSO-d6) = 0.98 (s, 9H), 4.26 (d, J = 10 Hz, 1H), 4.41 (d, J = 10 Hz, 1H), 5.73 (s, 1H), 7.22 (m, 1H), 7.31 (m, 1H), 7.47 (m, 1H), 7.76 (s, 1H), 8.92 (s, 1H) ppm. |
| 4 | S | O | 0 | 0 | tBu | H | 4-chloro-2-(methyl-sulfanyl)phenyl | ¹H NMR: δ (400 MHz, DMSO-d6) = 1.00 (s, 9H), 2.34 (s, 3H), 4.18 (d, J = 10 Hz, 1H), 4.37 (d, J = 10 Hz, 1H), 5.60 (s, 1H), 7.01 (d, J = 2 Hz, 1H), 7.08 (m, 1H), 7.14 (m, 1H), 7.86 (s, 1H), 8.92 (s, 1H) ppm. |
| 5 | S | O | 0 | 0 | tBu | H | 2-chloro-4-iodophenyl | logP 4.14[a]; [M + H]⁺ = 438. |
| 6 | S | O | 0 | 0 | iPr | H | 4-bromo-2-fluorophenyl | ¹H NMR: δ (400 MHz, DMSO-d6) = 0.81 (d, 3H), 0.90 (d, 3H), 2.27 (septet, 1H), 4.15 (d, 1H), 4.22 (d, 1H), 5.80 (s, 1H), 7.18 (t, 1H), 7.29-7.35 (m, 1H), 7.51 (dd, 1H), 7.78 (s, 1H), 8.95 (s, 1H) ppm; |
| 7 | S | O | 0 | 0 | MCP | H | 3,5-dibromophenyl | logP 4.03[a]; [M + H]⁺ = 434 |
| 8 | S | O | 0 | 0 | iPr | H | 4-bromo-2-chlorophenyl | ¹H NMR: δ (400 MHz, DMSO-d6) = 0.81 (d, 3H), 0.91 (d, 3H), 2.36 (septet, 1H), 4.13 (d, 1H), 4.19 (d, 1H), 5.80 (s, 1H), 7.13 (d, 1H), 7.47 (dd, 1H), 7.66 (d, 1H), 7.82 (s, 1H), 8.94 (s, 1H) ppm; |
| 9 | S | O | 0 | 0 | iPr | H | 4-chloro-2-(methyl-sulfanyl)phenyl | ¹H NMR: δ (400 MHz, DMSO-d6) = 0.80 (d, 3H), 0.91 (d, 3H), 2.38 (septet, 1H), 2.41 (s, 3H), 4.05 (d, 1H), 4.13 (d, 1H), 5.75 (s, 1H), 6.94 (d, 1H), 7.08-7.13 (m, 2H), 7.85 (s, 1H), 8.93 (s, 1H) ppm; |
| 10 | S | O | 0 | 0 | MCP | H | 4-iodo-2-methylphenyl | logP 3.88[a]; [M + H]⁺ = 416 |
| 11 | S | O | 0 | 0 | MCP | H | 4-bromo-3-chlorophenyl | ¹H NMR: δ (400 MHz, DMSO-d6) = 0.1-0.18 (m, 1H), 0.28-0.38 (m, 1H), 0.85-0.95 (m, 1H), 0.95 (s, 3H), 0.95-1.03 (m, 1H), 4.28 (d, 1H), 4.49 (d, 1H), 5.70 (s, 1H), 6.96 (dd, 1H), 7.35 (d, 1H), 7.64 (d, 1H), 7.85 (s, 1H), 8.98 (s, 1H) ppm |
| 12 | S | O | 0 | 0 | MCP | H | 4-bromo-3-fluorophenyl | logP 3.30[a]; [M + H]⁺ = 372, 374 |
| 13 | S | O | 0 | 0 | MCP | H | 4-bromo-3-(trifluoro-methyl)phenyl | logP 3.70[a]; [M + H]⁺ = 422, 424 |
| 14 | S | O | 0 | 0 | tBu | H | 2-methoxy-4-(trifluoro-methoxy)phenyl | logP 3.70[a]; [M + H]⁺ = 392. |
| 15 | S | O | 0 | 0 | MCP | H | 4-iodo-3-nitrophenyl | logP 3.11[a]; [M + H]⁺ = 447 |
| 16 | S | O | 0 | 0 | tBu | H | 3-fluoro-4-[(trifluoro-methyl)sulfanyl]phenyl | logP 3.96[a]; [M + H]⁺ = 396. |
| 17 | S | O | 0 | 0 | tBu | H | 3-methyl-4-(methyl-sulfonyl)phenyl | logP 2.21[a]; [M + H]⁺ = 370. |
| 18 | S | O | 0 | 0 | tBu | H | 3-methyl-4-(methyl-sulfinyl)phenyl | logP 1.90[a]; [M + H]⁺ = 354. |
| 19 | S | O | 0 | 0 | tBu | H | 2-methyl-4-[(trifluoro-methyl)sulfonyl]phenyl | logP 3.63[a]; [M + H]⁺ = 424. |
| 20 | S | O | 0 | 0 | tBu | H | 2-methoxy-4-[(trifluoro-methyl)sulfonyl]phenyl | logP 3.37[a]; [M + H]⁺ = 440. |
| 21 | S | O | 0 | 0 | tBu | H | 3-chloro-4-[(trifluoro-methyl)sulfonyl]phenyl | logP 4.31[a]; [M + H]⁺ = 412. |
| 22 | S | O | 0 | 0 | tBu | H | 3-methyl-4-[(trifluor-methyl)sulfanyl]phenyl | logP 4.35[a]; [M + H]⁺ = 392. |
| 23 | S | O | 0 | 0 | tBu | H | 2-methyl-4-[(trifluoro-methyl)sulfanyl]phenyl | logP 4.43[a]; [M + H]⁺ = 392. |
| 24 | S | O | 0 | 0 | tBu | H | 3-chloro-4-(trifluoro-methoxy)phenyl | logP 4.02[a]; [M + H]⁺ = 396. |
| 25 | S | O | 0 | 0 | tBu | H | 4-chloro-2-methylphenyl | logP 3.77[a]; [M + H]⁺ = 326. |
| 26 | S | O | 0 | 0 | tBu | H | 4-chloro-2-fluorphenyl | logP 3.37[a]; [M + H]⁺ = 330. |
| 27 | S | O | 0 | 0 | tBu | H | 4-chloro-3-methylphenyl | logP 3.74[a]; [M + H]⁺ = 326. |
| 28 | S | O | 0 | 0 | tBu | H | 3-methyl-4-(methyl-sulfanyl)phenyl | logP 3.63[a]; [M + H]⁺ = 338. |
| 29 | S | O | 0 | 0 | tBu | H | 2-chloro-4-(trifluor-methoxy)phenyl | logP 4.10[a]; [M + H]⁺ = 396. |

TABLE 1-continued

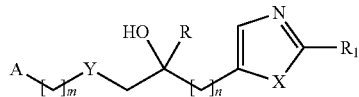

(I)

| No. | X | Y | m | n | R | R¹ | A | Physical data |
|---|---|---|---|---|---|---|---|---|
| 30 | S | O | 0 | 0 | tBu | H | 3-chlorobiphenyl-4-yl | ¹H NMR: δ (400 MHz, DMSO-d6) = 1.04 (s, 9H), 4.29 (d, J = 10 Hz, 1H), 4.43 (d, J = 10 Hz, 1H), 5.73 (s, 1H), 7.27 (d, J = 9 Hz, 1H), 7.34 (m, 1H), 7.44 (m, 2H), 7.61 (m, 3H), 7.71 (d, J = 2 Hz, 1H), 7.87 (s, 1H), 8.94 (s, 1H) ppm. |
| 31 | S | — | 0 | 0 | tBu | H | 2,4-difluorophenyl | logP 3.04[a]; [M + H]+ = 298. |
| 32 | S | O | 0 | 0 | MCP | H | 4-bromo-2-fluorophenyl | logP 3.32[a]; [M + H]+ = 372, 374 |
| 33 | S | O | 0 | 0 | tBu | H | 2,4-dichlorophenyl | logP 3.84[a] |
| 34 | S | O | 0 | 0 | tBu | H | 2,4-difluorophenyl | logP 2.98[a] |
| 35 | S | O | 0 | 0 | MCP | H | 4-bromo-2-methoxyphenyl | logP 3.26[a] |
| 36 | S | O | 0 | 0 | MCP | H | 4-bromo-3-methoxyphenyl | logP 3.16[a] |
| 37 | S | O | 0 | 0 | tBu | H | 4-chloro-2-(trifluoromethyl)phenyl | logP 3.96[a] |
| 38 | S | O | 0 | 0 | TFCP | H | 2-fluoro-4-iodophenyl | |
| 39 | S | O | 0 | 0 | tBu | H | 3,4-dichlorophenyl | logP 3.72[a] |
| 40 | S | O | 0 | 0 | TFCP | H | 4-bromo-2-methylphenyl | |
| 41 | S | O | 0 | 0 | tBu | H | 3-bromo-4-(trifluoromethoxy)phenyl | logP 4.12[a] |
| 42 | S | O | 0 | 0 | tBu | H | 2-methyl-4-(trifluoromethoxy)phenyl | logP 4.12[a] |
| 43 | S | — | 0 | 1 | CCP | Cl | 2,4-dichlorophenyl | |
| 1 | S | O | 0 | 0 | tBu | H | 2-fluoro-4-iodophenyl | ¹H NMR: δ (400 MHz, DMSO-d6) = 0.98 (s, 9H), 4.25 (d, J = 10 Hz, 1H), 4.40 (d, J = 10 Hz, 1H), 5.75 (s, 1H), 7.07 (m, 1H), 7.47 (m, 1H), 7.57 (m, 1H), 7.76 (s, 1H), 8.93 (s, 1H) ppm. |
| 2 | S | O | 0 | 0 | tBu | H | 4-bromo-2-chlorophenyl | ¹H NMR: δ (400 MHz, DMSO-d6) = 0.97 (s, 9H), 4.25 (d, J = 10 Hz, 1H), 4.38 (d, J = 10 Hz, 1H), 5.69 (s, 1H), 7.17 (d, J = 9 Hz, 1H), 7.48 (dd, J = 9 Hz, 2 Hz, 1H), 7.63 (d, J = 2 Hz, 1H), 7.81 (s, 1H), 8.92 (s, 1H) ppm. |
| 3 | S | O | 0 | 0 | tBu | H | 4-bromo-2-fluorophenyl | ¹H NMR: δ (400 MHz, DMSO-d6) = 0.98 (s, 9H), 4.26 (d, J = 10 Hz, 1H), 4.41 (d, J = 10 Hz, 1H), 5.73 (s, 1H), 7.22 (m, 1H), 7.31 (m, 1H), 7.47 (m, 1H), 7.76 (s, 1H), 8.92 (s, 1H) ppm. |
| 4 | S | O | 0 | 0 | tBu | H | 4-chloro-2-(methyl-sulfanyl)phenyl | ¹H NMR: δ (400 MHz, DMSO-d6) = 1.00 (s, 9H), 2.34 (s, 3H), 4.18 (d, J = 10 Hz, 1H), 4.37 (d, J = 10 Hz, 1H), 5.60 (s, 1H), 7.01 (d, J = 2 Hz, 1H), 7.08 (m, 1H), 7.14 (m, 1H), 7.86 (s, 1H), 8.92 (s, 1H) ppm. |
| 5 | S | O | 0 | 0 | tBu | H | 2-chloro-4-iodophenyl | logP 4.14[a]; [M + H]+ = 438. |
| 6 | S | O | 0 | 0 | iPr | H | 4-bromo-2-fluorophenyl | ¹H NMR: δ (400 MHz, DMSO-d6) = 0.81 (d, 3H), 0.90 (d, 3H), 2.27 (septet, 1H), 4.15 (d, 1H), 4.22(d, 1H), 5.80 (s, 1H), 7.18 (t, 1H), 7.29-7.35 (m, 1H), 7.51 (dd, 1H), 7.78 (s, 1H), 8.95 (s, 1H) ppm; |
| 7 | S | O | 0 | 0 | MCP | H | 3,5-dibromophenyl | logP 4.03[a]; [M + H]+ = 434 |
| 8 | S | O | 0 | 0 | iPr | H | 4-bromo-2-chlorophenyl | ¹H NMR: δ (400 MHz, DMSO-d6) = 0.81 (d, 3H), 0.91 (d, 3H), 2.36 (septet, 1H), 4.13 (d, 1H), 4.19 (d, 1H), 5.80 (s, 1H), 7.13 (d, 1H), 7.47 (dd, 1H), 7.66 (d, 1H), 7.82 (s, 1H), 8.94 (s, 1H) ppm; |
| 9 | S | O | 0 | 0 | iPr | H | 4-chloro-2-(methyl-sulfanyl)phenyl | ¹H NMR: δ (400 MHz, DMSO-d6) = 0.80 (d, 3H), 0.91 (d, 3H), 2.38 (septet, 1H), 2.41 (s, 3H), 4.05 (d, 1H), 4.13 (d, 1H), 5.75 (s, 1H), 6.94 (d, 1H), 7.08-7.13 (m, 2H), 7.85 (s, 1H), 8.93 (s, 1H) ppm; |
| 10 | S | O | 0 | 0 | MCP | H | 4-iodo-2-methylphenyl | logP 3.88[a]; [M + H]+ = 416 |
| 11 | S | O | 0 | 0 | MCP | H | 4-bromo-3-chlorophenyl | ¹H NMR: δ (400 MHz, DMSO-d6) = 0.1-0.18 (m, 1H), 0.28-0.38 (m, 1H), 0.85-0.95 (m, 1H), 0.95 (s, 3H), 0.95-1.03 (m, 1H), 4.28 (d, 1H), 4.49 (d, 1H), 5.70 (s, 1H), 6.96 (dd, 1H), 7.35 (d, 1H), 7.64 (d, 1H), 7.85 (s, 1H), 8.98 (s, 1H) ppm |

TABLE 1-continued (I)

| No. | X | Y | m | n | R | R[1] | A | Physical data |
|---|---|---|---|---|---|---|---|---|
| 12 | S | O | 0 | 0 | MCP | H | 4-bromo-3-fluorophenyl | logP 3.30[a]; [M + H]+ = 372, 374 |
| 13 | S | O | 0 | 0 | MCP | H | 4-bromo-3-(trifluoromethyl)phenyl | logP 3.70[a]; [M + H]+ = 422, 424 |
| 14 | S | O | 0 | 0 | tBu | H | 2-methoxy-4-(trifluoromethoxy)phenyl | logP 3.70[a]; [M + H]+ = 392. |
| 15 | S | O | 0 | 0 | MCP | H | 4-iodo-3-nitrophenyl | logP 3.11[a]; [M + H]+ = 447 |
| 16 | S | O | 0 | 0 | tBu | H | 3-fluoro-4-[(trifluoromethyl)sulfanyl]phenyl | logP 3.96[a]; [M + H]+ = 396. |
| 17 | S | O | 0 | 0 | tBu | H | 3-methyl-4-(methylsulfonyl)phenyl | logP 2.21[a]; [M + H]+ = 370. |
| 18 | S | O | 0 | 0 | tBu | H | 3-methyl-4-(methylsulfinyl)phenyl | logP 1.90[a]; [M + H]+ = 354. |
| 19 | S | O | 0 | 0 | tBu | H | 2-methyl-4-[(trifluoromethyl)sulfonyl]phenyl | logP 3.63[a]; [M + H]+ = 424. |
| 20 | S | O | 0 | 0 | tBu | H | 2-methoxy-4-[(trifluoromethyl)sulfonyl]phenyl | logP 3.37[a]; [M + H]+ = 440. |
| 21 | S | O | 0 | 0 | tBu | H | 3-chloro-4-[(trifluoromethyl)sulfanyl]phenyl | logP 4.31[a]; [M + H]+ = 412. |
| 22 | S | O | 0 | 0 | tBu | H | 3-methyl-4-[(trifluoromethyl)sulfanyl]phenyl | logP 4.35[a]; [M + H]+ = 392. |
| 23 | S | O | 0 | 0 | tBu | H | 2-methyl-4-[(trifluoromethyl)sulfanyl]phenyl | logP 4.43[a]; [M + H]+ = 392. |
| 24 | S | O | 0 | 0 | tBu | H | 3-chloro-4-(trifluoromethoxy)phenyl | logP 4.02[a]; [M + H]+ = 396. |
| 25 | S | O | 0 | 0 | tBu | H | 4-chloro-2-methylphenyl | logP 3.77[a]; [M + H]+ = 326. |
| 26 | S | O | 0 | 0 | tBu | H | 4-chloro-2-fluorophenyl | logP 3.37[a]; [M + H]+ = 330. |
| 27 | S | O | 0 | 0 | tBu | H | 4-chloro-3-methylphenyl | logP 3.74[a]; [M + H]+ = 326. |
| 28 | S | O | 0 | 0 | tBu | H | 3-methyl-4-(methylsulfanyl)phenyl | logP 3.63[a]; [M + H]+ = 338. |
| 29 | S | O | 0 | 0 | tBu | H | 2-chloro-4-(trifluoromethoxy)phenyl | logP 4.10[a]; [M + H]+ = 396. |
| 30 | S | O | 0 | 0 | tBu | H | 3-chlorobiphenyl-4-yl | 1H NMR: δ (400 MHz, DMSO-d6) = 1.04 (s, 9H), 4.29 (d, J = 10 Hz, 1H), 4.43 (d, J = 10 Hz, 1H), 5.73 (s, 1H), 7.27 (d, J = 9Hz, 1H), 7.34 (m, 1H), 7.44 (m, 2H), 7.61 (m, 3H), 7.71 (d, J = 2 Hz, 1H), 7.87 (s, 1H), 8.94 (s, 1H) ppm. |
| 31 | S | — | 0 | 0 | tBu | H | 2,4-difluorophenyl | logP 3.04[a]; [M + H]+ = 298. |
| 32 | S | O | 0 | 0 | MCP | H | 4-bromo-2-fluorophenyl | logP 3.32[a]; [M + H]+ = 372, 374 |
| 33 | S | O | 0 | 0 | tBu | H | 2,4-dichlorophenyl | logP 3.84[a] |
| 34 | S | O | 0 | 0 | tBu | H | 2,4-difluorophenyl | logP 2.98[a] |
| 35 | S | O | 0 | 0 | MCP | H | 4-bromo-2-methoxyphenyl | logP 3.26[a] |
| 36 | S | O | 0 | 0 | MCP | H | 4-bromo-3-methoxyphenyl | logP 3.16[a] |
| 37 | S | O | 0 | 0 | tBu | H | 4-chloro-2-(trifluoromethyl)phenyl | logP 3.96[a] |
| 38 | S | O | 0 | 0 | TFCP | H | 2-fluoro-4-iodophenyl | logP 3.72[a] |
| 39 | S | O | 0 | 0 | tBu | H | 3,4-dichlorophenyl | logP 3.72[a] | iPr = isopropyl,
tBu = tert-butyl,
DFMP = 1,3-difluoro-2-methylpropan-2-yl,
CCP = 1-chlorocyclopropyl,
FCP = 1-fluorocyclopropyl,
MCP = 1-methylcyclopropyl,
TFCP = 1-(trifluoromethyl)cyclopropyl,
CCP = 1-chlorocyclopropyl.

The log P values were measured in accordance with EEC Directive 79/831 Annex V.A8 by HPLC (High Performance Liquid Chromatography) using reversed-phase columns (C18) by the following methods:

[a] The LC-MS determination in the acidic range is effected at pH 2.7 with 0.1% aqueous formic acid and acetonitrile (contains 0.1% formic acid) as eluents; linear gradient from 10% acetonitrile to 95% acetonitrile.

[b] The LC-MS determination in the acidic range is effected at pH 2.3 with 0.1% aqueous phosphoric acid and acetonitrile (contains 0.1% phosphoric acid) as eluents; linear gradient from 10% acetonitrile to 95% acetonitrile.

Further NMR Data of Selected Examples

The 1H NMR data of the selected examples which follow are noted in the form of 1H NMR peak lists. For each signal peak, first the δ value in ppm and then the signal intensity in brackets are listed, separated by a space. The δ-signal intensity value pairs of different signal peaks are listed separated from one another by semicolons. The peak list of one example therefore takes the form of:

δ₁ (intensity₁); δ₂ (intensity₂); ... ; δᵢ (intensityᵢ); ... ; δₙ (intensityₙ)

The solvent in which the NMR spectrum was recorded is listed in square brackets after the Example number and before the NMR peak list. A detailed description of the presentation of NMR data in the form of peak lists can be found in the publication "Citation of NMR Peaklist Data within Patent Applications" (cf. Research Disclosure Database Number 564025, 2011, 16 Mar. 2011.

Example 33 [DMSO-D₆] 8.9252 (1.70); 7.8174 (1.99); 7.5363 (1.28); 7.5299 (1.35); 7.3763 (0.66); 7.3698 (0.61); 7.3541 (0.91); 7.3476 (0.85); 7.2447 (1.41); 7.2224 (1.01); 5.7075 (2.38); 4.4053 (0.78); 4.3804 (1.08); 4.2752 (1.06); 4.2503 (0.77); 3.3076 (15.73); 2.5109 (2.04); 2.5066 (3.68); 2.5022 (4.70); 2.4978 (3.29); 2.4935 (1.59); 1.0097 (16.00); 0.9766 (0.32); −0.0002 (0.55)
Example 34 [DMSO-D₆] 8.9306 (1.68); 7.7749 (1.98); 7.7738 (1.88); 7.2648 (0.56); 7.2549 (0.60); 7.2413 (0.68); 7.2360 (0.69); 7.2296 (0.52); 7.2170 (0.39); 7.2146 (0.39); 7.2067 (0.32); 6.9955 (0.36); 6.9931 (0.39); 5.7292 (2.49); 4.4182 (0.81); 4.3934 (1.05); 4.2526 (1.04); 4.2278 (0.80); 3.3064 (20.14); 2.5101 (2.51); 2.5059 (4.55); 2.5014 (5.86); 2.4971 (4.15); 2.4928 (2.04); 2.0856 (0.98); 0.9834 (16.00)
Example 35 [DMSO-D₆] 8.8319 (0.91); 8.8306 (0.83); 7.7553 (1.08); 7.7539 (0.98); 7.0090 (0.61); 7.0042 (0.65); 6.9249 (0.70); 6.9199 (0.72); 6.9139 (1.00); 5.4730 (0.53); 4.2354 (0.44); 4.2106 (0.56); 4.0778 (0.55); 4.0530 (0.43); 3.6439 (3.78); 3.1747 (16.00); 2.3756 (1.80); 2.3714 (3.19); 2.3669 (4.02); 2.3626 (2.79); 2.3583 (1.34); 1.2644 (2.79); 0.8283 (2.72)
Example 38 [DMSO-D₆] 9.0525 (1.82); 9.0512 (1.78); 7.9899 (1.92); 7.6233 (0.67); 7.6182 (0.70); 7.5966 (0.67); 7.5915 (0.71); 7.5079 (0.42); 7.5043 (0.52); 7.4865 (0.48); 7.4828 (0.58); 7.4782 (0.42); 7.1953 (0.57); 7.1732 (1.01); 7.1511 (0.51); 6.4388 (2.18); 4.5935 (0.42); 4.5675 (1.05); 4.5406 (0.99); 4.5145 (0.37); 3.3034 (161.71); 2.8902 (0.40); 2.7307 (0.34); 2.6690 (0.34); 2.5391 (0.82); 2.5088 (19.00); 2.5044 (34.29); 2.5000 (43.96); 2.4956 (30.41); 2.4912 (14.67); 1.9867 (0.64); 1.4345 (0.36); 1.3984 (16.00); 1.1749 (0.41); 1.0343 (0.40); 1.0215 (0.36); 1.0176 (0.36); 0.9072 (0.35); 0.9023 (0.35); 0.8941 (0.33); 0.8901 (0.40); −0.0002 (2.98)
Example 39 [DMSO-D₆] 8.9293 (1.66); 8.9252 (1.50); 7.7499 (2.01); 7.7460 (1.81); 7.4968 (1.06); 7.4912 (1.04); 7.4745 (1.14); 7.4689 (1.09); 7.2936 (1.19); 7.2878 (1.73); 7.2812 (1.10); 6.9625 (0.67); 6.9567 (0.95); 6.9498 (0.63); 6.9402 (0.64); 6.9343 (0.87); 6.9274 (0.54); 5.7478 (2.18); 5.7423 (2.10); 4.4855 (0.85); 4.4811 (0.79); 4.4606 (1.02); 4.4563 (0.92); 4.2260 (1.00); 4.2216 (0.93); 4.2012 (0.86); 4.1966 (0.78); 3.3176 (23.07); 3.3121 (23.19); 2.5070 (8.01); 2.5028 (7.25); 1.4032 (6.86); 1.3977 (6.63); 0.9815 (16.00); 0.9767 (15.10); 0.0056 (0.33); −0.0002 (0.34)
Example 40 [DMSO-D₆] 9.0508 (0.67); 8.0110 (0.71); 7.3414 (0.77); 7.3223 (0.35); 6.3728 (0.86); 5.7461 (16.00); 3.4276 (0.38); 3.3103 (878.85); 3.2874 (8.38); 3.1792 (0.41); 2.6738 (0.79); 2.6694 (1.06); 2.6650 (0.82); 2.5393 (2.27); 2.5090 (57.98); 2.5048 (103.51); 2.5004 (131.54); 2.4960 (92.07); 2.4918 (44.88); 2.3315 (0.71); 2.3270 (0.91); 2.3223 (0.65); 2.1489 (1.89); −0.0002 (20.21); −0.0084 (0.67)
Example 41 [DMSO-D₆] 8.9346 (1.09); 7.7564 (1.50); 7.4376 (1.43); 7.4302 (1.65); 7.4267 (0.74); 7.4233 (0.68); 7.4037 (0.67); 7.4006 (0.68); 7.0487 (0.80); 7.0413 (0.77); 7.0260 (0.72); 7.0185 (0.71); 5.7665 (1.41); 4.5124 (0.83); 4.4875 (0.98); 4.2367 (0.96); 4.2117 (0.84); 3.3287 (8.45); 2.5106 (4.28); 2.5065 (8.31); 2.5022 (11.54); 2.4980 (8.03); 2.4938 (4.03); 0.9767 (16.00); −0.0002 (3.34)
Example 42 [DMSO-D₆] 8.9289 (1.63); 7.7418 (1.67); 7.1351 (0.39); 7.1130 (1.59); 7.0806 (1.15); 7.0598 (0.62); 5.7043 (2.43); 4.3361 (0.60); 4.3111 (1.15); 4.2759 (1.17); 4.2515 (0.63); 3.3230 (186.57); 3.3183 (185.48); 3.2963 (2.14); 2.6791 (0.65); 2.6748 (1.23); 2.6699 (1.77); 2.6658 (1.28); 2.5403 (2.60); 2.5233 (2.96); 2.5052 (190.70); 2.5011 (256.80); 2.4975 (177.76); 2.4670 (0.52); 2.3370 (0.65); 2.3324 (1.32); 2.3277 (1.67); 2.3232 (1.28); 1.9428 (5.19); 1.3353 (0.32); 1.2981 (0.34); 1.2589 (0.48); 1.2435 (0.53); 1.2354 (0.74); 1.0053 (16.00); 0.9754 (0.47); 0.9552 (0.33); 0.9115 (0.42); 0.8852 (1.24); 0.8412 (0.85); 0.1457 (0.33); 0.0080 (2.35); −0.0002 (85.85); −0.0085 (2.63); −0.1498 (0.38)
Example 43 [DMSO-D₆] 7.6729 (0.36); 7.6694 (0.37); 7.5753 (0.40); 7.5616 (2.54); 7.5578 (4.26); 7.5434 (2.41); 7.4583 (3.60); 7.4418 (0.57); 7.4379 (0.32); 7.4032 (1.47); 7.3995 (1.41); 7.3893 (1.26); 7.3856 (1.21); 6.7796 (0.55); 5.9223 (0.32); 5.9136 (0.35); 5.3362 (0.34); 5.2956 (3.46); 5.1833 (0.33); 5.1144 (0.36); 4.0600 (0.54); 4.0517 (0.54); 3.4593 (1.60); 3.4360 (1.76); 3.4159 (1.33); 3.3910 (1.46); 3.3496 (50.10); 3.0106 (1.61); 2.9872 (1.44); 2.8750 (1.35); 2.8500 (1.25); 2.5251 (0.35); 2.5220 (0.44); 2.5189 (0.51); 2.5098 (9.60); 2.5070 (19.67); 2.5041 (26.50); 2.5011 (19.54); 2.4983 (9.39); 1.3967 (16.00); 1.3859 (0.69); 1.2709 (0.42); 1.2679 (0.40); 0.9610 (0.38); 0.9586 (0.41); 0.9525 (0.66); 0.9433 (0.66); 0.9408 (0.75); 0.9323 (0.64); 0.9171 (0.60); 0.9087 (0.71); 0.9066 (0.75); 0.8977 (0.72); 0.8911 (0.36); 0.8886 (0.42); 0.8798 (0.36); 0.7468 (0.40); 0.7374 (0.51); 0.7356 (0.52); 0.7284 (0.79); 0.7196 (0.67); 0.7178 (0.70); 0.7092 (0.46); 0.6315 (0.49); 0.6233 (0.60); 0.6205 (0.61); 0.6141 (0.61); 0.6124 (0.65); 0.6056 (0.45); 0.6026 (0.48); 0.5938 (0.33); −0.0002 (1.48)

Use Examples

Example A

*Blumeria graminis* Test (Barley)/Protective

Solvent: 49 parts by weight of N,N-dimethylacetamide
Emulsifier: 1 part by weight of alkylaryl polyglycol ether To produce an appropriate active ingredient formulation, 1 part by weight of active ingredient is mixed with the specified amounts of solvent and emulsifier, and the concentrate is diluted with water to the desired concentration. To test for protective activity, young plants are sprayed with the formulation of active ingredient at the stated application rate. After the spray coating has dried on, the plants are dusted with spores of *Blumeria graminis* f sp. *hordei*. The plants are placed in a greenhouse at a temperature of about 18° C. and a relative air humidity of about 80% to promote the development of mildew pustules. Evaluation follows 7 days after the inoculation. 0% means an efficacy which corresponds to that of the control, whereas an efficacy of 100% means that no infection is observed. In this test, the following inventive compounds, at an active ingredient concentration of 500 ppm, show an efficacy of 70% or more.

TABLE A

*Blumeria graminis* test (barley)/protective

| No. | Active Ingredient | Application rate (ppm) | Efficacy (%) |
|---|---|---|---|
| 1 | 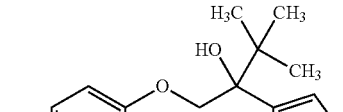 | 500 | 100 |
| 2 | 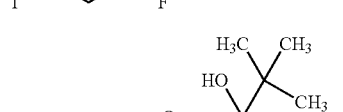 | 500 | 100 |
| 3 | 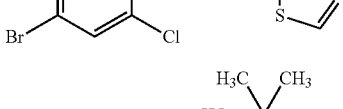 | 500 | 100 |

Example B

*Leptosphaeria nodorum* Test (Wheat)/Protective

Solvent: 49 parts by weight of N,N-dimethylacetamide
Emulsifier: 1 part by weight of alkylaryl polyglycol ether To produce an appropriate active ingredient formulation, 1 part by weight of active ingredient is mixed with the specified amounts of solvent and emulsifier, and the concentrate is diluted with water to the desired concentration. To test for protective activity, young plants are sprayed with the formulation of active ingredient at the stated application rate. After the spray coating has dried on, the plants are sprayed with spores with a spore suspension of *Leptosphaeria nodorum*. The plants remain in an incubation cabin at 20° C. and 100% relative air humidity for 48 hours. The plants are placed in a greenhouse at a temperature of about 22° C. and a relative air humidity of about 80%. Evaluation follows 8 days after the inoculation. 0% means an efficacy which corresponds to that of the control, whereas an efficacy of 100% means that no infection is observed. In this test, the following inventive compounds, at an active ingredient concentration of 500 ppm, show an efficacy of 70% or more.

TABLE B

*Leptosphaeria nodorum* test (wheat)/protective

| No. | Active Ingredient | Application rate (ppm) | Efficacy (%) |
|---|---|---|---|
| 1 |  | 500 | 100 |
| 2 | 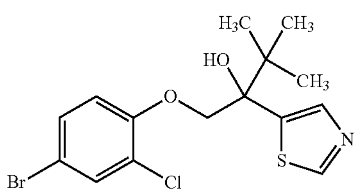 [SMILES: CC(C)(C)C(O)(COc1ccc(Br)cc1Cl)c1cncs1]  | 500 | 92 |
| 3 | 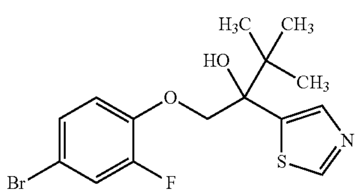  | 500 | 100 |

Example C

*Puccinia triticina* Test (Wheat)/Protective

Solvent: 49 parts by weight of N,N-dimethylacetamide
Emulsifier: 1 part by weight of alkylaryl polyglycol ether To produce an appropriate active ingredient formulation, 1 part by weight of active ingredient is mixed with the specified amounts of solvent and emulsifier, and the concentrate is diluted with water to the desired concentration. To test for protective activity, young plants are sprayed with the formulation of active ingredient at the stated application rate. After the spray coating has dried on, the plants are sprayed with spores with a spore suspension of *Puccinia triticina*. The plants remain in an incubation cabin at 20° C. and 100% relative air humidity for 48 hours. The plants are placed in a greenhouse at a temperature of about 20° C. and a relative air humidity of about 80%. Evaluation follows 8 days after the inoculation. 0% means an efficacy which corresponds to that of the control, whereas an efficacy of 100% means that no infection is observed. In this test, the following inventive compounds, at an active ingredient concentration of 500 ppm, show an efficacy of 70% or more.

TABLE C

*Puccinia triticina* test (wheat)/protective

| No. | Active Ingredient | Application rate (ppm) | Efficacy (%) |
|---|---|---|---|
| 1 |  | 500 | 100 |
| 2 | 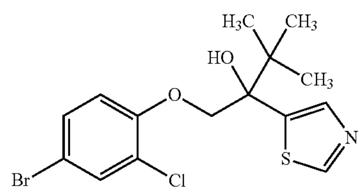 [SMILES: CC(C)(C)C(O)(COc1ccc(Br)cc1Cl)c1cncs1]  | 500 | 95 |
| 3 | 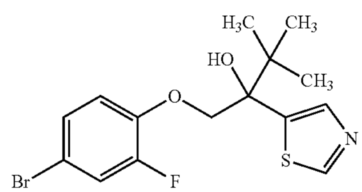  | 500 | 100 |

Example D

*Uromyces* Test (Bean)/Protective

Solvent: 24.5 parts by weight of acetone
24.5 parts by weight of dimethylacetamide
Emulsifier: 1 part by weight of alkylaryl polyglycol ether To produce an appropriate active ingredient formulation, 1 part by weight of active ingredient is mixed with the specified amounts of solvent and emulsifier, and the concentrate is diluted with water to the desired concentration. To test for protective activity, young plants are sprayed with the active ingredient formulation at the stated application rate. After the spray coating has dried on, the plants are inoculated with an aqueous spore suspension of the bean rust pathogen *Uromyces appendiculatus* and then remain in an incubation cabin at about 20° C. and 100% relative air humidity for 1 day. The plants are then placed in the greenhouse at about 21° C. and a relative air humidity of about 90%. Evaluation follows 10 days after the inoculation. 0% means an efficacy which corresponds to that of the control, whereas an efficacy of 100% means that no infection is observed. In this test, the following inventive compounds, at an active ingredient concentration of 100 ppm, show an efficacy of 70% or more.

TABLE D

Uromyces test (bean)/protective

| No. | Active Ingredient | Application rate (ppm) | Efficacy (%) |
|---|---|---|---|
| 1 | (H3C, CH3, HO, O, I, F, CH3, thiazole structure) | 100 | 100 |

Example E

Venturia Test (Apple)/Protective

Solvent: 24.5 parts by weight of acetone
24.5 parts by weight of dimethylacetamide
Emulsifier: 1 part by weight of alkylaryl polyglycol ether To produce an appropriate active ingredient formulation, 1 part by weight of active ingredient is mixed with the specified amounts of solvent and emulsifier, and the concentrate is diluted with water to the desired concentration. To test for protective activity, young plants are sprayed with the active ingredient formulation at the stated application rate. After the spray coating has dried on, the plants are inoculated with an aqueous conidia suspension of the apple scab pathogen Venturia inaequalis and then remain in an incubation cabin at about 20° C. and 100% relative air humidity for 1 day. The plants are then placed in a greenhouse at about 21° C. and a relative air humidity of about 90%. Evaluation follows 10 days after the inoculation. 0% means an efficacy which corresponds to that of the control, whereas an efficacy of 100% means that no infection is observed. In this test, the following inventive compounds, at an active ingredient concentration of 100 ppm, show an efficacy of 70% or more.

TABLE E

Venturia test (apple)/protective

| No. | Active Ingredient | Application rate (ppm) | Efficacy (%) |
|---|---|---|---|
| 1 | (H3C, CH3, HO, O, I, F, CH3, thiazole structure) | 100 | 97 |

The invention claimed is:

1. A compound of formula (I)

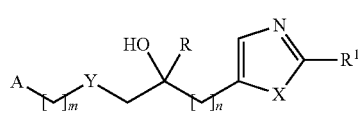

in which
X is O or S,
Y is O, —CH$_2$— or a direct bond,
m is 0 or 1,
n is 0 or 1,
R is alkyl, alkenyl, cycloalkyl or aryl, each of which is optionally substituted,
R$^1$ is hydrogen, SH, alkylthio, alkoxy, halogen, haloalkyl, haloalkylthio, haloalkoxy, cyano, nitro or Si(alkyl)$_3$,
A is 2- and 4-Z substituted phenyl, wherein the two Z substituents are identical or different, or is 3- and 4-Z substituted phenyl, wherein the two Z substituents are identical or different,
Z is halogen, cyano, nitro, OH, SH, C(alkyl)(=NOalkyl), $C_3$-$C_7$-cycloalkyl, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, formyl, $C_2$-$C_5$-alkylcarbonyl, $C_2$-$C_5$-haloalkylcarbonyl, $C_2$-$C_5$-alkoxycarbonyl, $C_2$-$C_5$-haloalkoxycarbonyl, $C_3$-$C_6$-alkenyloxy, $C_3$-$C_6$-alkynyloxy, $C_2$-$C_5$-alkylcarbonyloxy, $C_2$-$C_5$-haloalkylcarbonyloxy, trialkylsilyl, or phenyl, phenoxy or phenylthio, each of which is optionally monosubstituted with halogen, $C_1$-$C_4$-alkyl, $C_1$-$C_4$-haloalkyl, $C_1$-$C_4$-alkoxy or $C_2$-$C_4$-alkylcarbonyl, and wherein one of the Z substituents is bromine or iodine,
and salts thereof.

2. The compound of claim 1, in which
X is O or S,
Y is O, —CH$_2$— or a direct bond,
m is 0 or 1,
n is 0 or 1,
R is optionally branched $C_3$-$C_7$-alkyl, optionally branched $C_1$-$C_8$-haloalkyl, optionally branched $C_2$-$C_7$-alkenyl, optionally branched $C_2$-$C_7$-haloalkenyl, $C_3$-$C_7$-cycloalkyl, which is optionally substituted with halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-haloalkylthio or $C_1$-$C_4$-alkylthio, or phenyl which is optionally substituted with mono-halogen, di-halogen, tri-halogen, or $C_1$-$C_4$-alkyl,
R$^1$ is hydrogen, SH, $C_1$-$C_4$-alkylthio, $C_1$-$C_4$-alkoxy or halogen, and
Z is halogen, cyano, nitro, C($C_1$-$C_5$-alkyl)(=NO($C_1$-$C_5$-alkyl)), $C_3$-$C_6$-cycloalkyl, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_2$-$C_4$-alkenyl, $C_2$-$C_4$-alkynyl, $C_1$-$C_4$-alkylsulphinyl, $C_1$-$C_4$-alkylsulphonyl, $C_2$-$C_5$-alkylcarbonyl, $C_2$-$C_5$-alkoxycarbonyl, $C_3$-$C_6$-alkenyloxy, $C_3$-$C_6$-alkynyloxy, $C_2$-$C_5$-alkylcarbonyloxy, or phenyl, phenoxy or phenylthio, each of which is monosubstituted with halogen, $C_1$-$C_4$-alkyl, $C_1$-$C_4$-haloalkyl, $C_1$-$C_4$-alkoxy or $C_2$-$C_4$-alkylcarbonyl.

3. A method for controlling phytopathogenic harmful fungi, comprising applying a compound of claim 1 to the phytopathogenic harmful fungi, their habitat, or combinations thereof.

4. A composition for controlling phytopathogenic harmful fungi, comprising the compound of claim 1 and an extender, a surfactant, or combinations thereof.

5. The composition of claim 4, further comprising at least one further active ingredient selected from the group consisting of insecticides, attractants, sterilants, bactericides, acaricides, nematicides, fungicides, growth regulators, herbicides, fertilizers, safeners, semiochemicals, and combinations thereof.

6. A method of inhibiting vegetative growth comprising applying the compound according to claim 1 to a seed, a plant, parts of a plant, fruit of a plant, soil surrounding a plant, or combinations thereof.

7. The method according to claim 6, wherein the plant is a transgenic plant.

8. The method according to claim 6, wherein the seed is from a transgenic plant.

9. The compound of claim 1, wherein

R is optionally branched $C_3$-$C_5$-alkyl, optionally branched $C_1$-$C_6$-haloalkyl, optionally branched $C_3$-$C_5$-alkenyl, optionally branched $C_3$-$C_5$-haloalkenyl, or $C_3$-$C_6$-cycloalkyl, which is optionally substituted with halogen, $C_1$-$C_4$-alkyl, $C_1$-$C_4$-haloalkyl, $C_1$-$C_4$-haloalkoxy, $C_1$-$C_4$-alkoxy, or $C_1$-$C_4$-haloalkylthio; and $R^1$ is hydrogen, SH, methylthio, ethylthio, methoxy, ethoxy, fluorine, chlorine, bromine, or iodine.

10. The compound of claim 1, wherein

R is tert-butyl, isopropyl, 1-chlorocyclopropyl, 1-fluorocyclopropyl, 1-methylcyclopropyl, 1-methoxycyclopropyl, 1-methylthiocyclopropyl, 1-trifluoromethylcyclopropyl, (3E)-4-chloro-2-methylbut-3-en-2-yl, or $C_1$-$C_4$-haloalkyl.

11. The compound of claim 1, wherein the compound is:

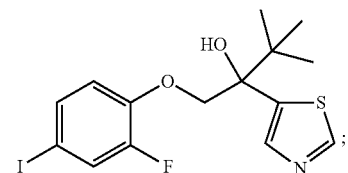

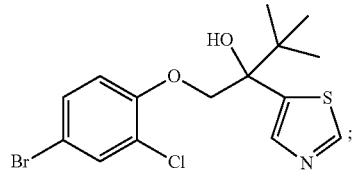

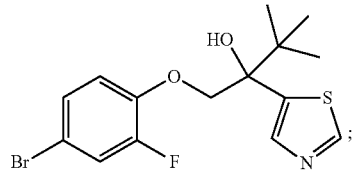

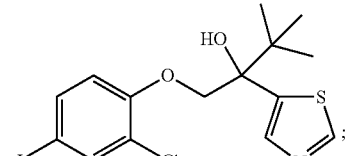

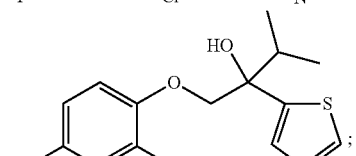

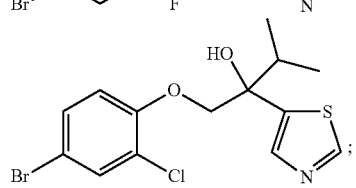

-continued

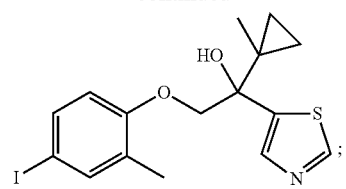

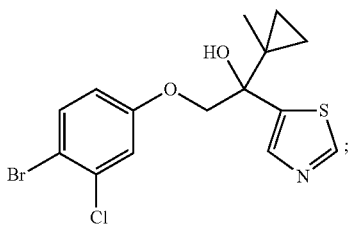

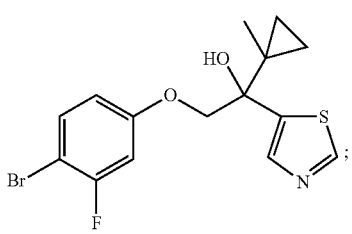

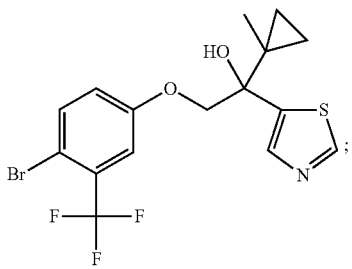

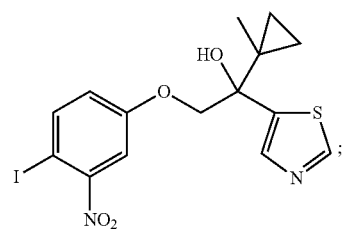

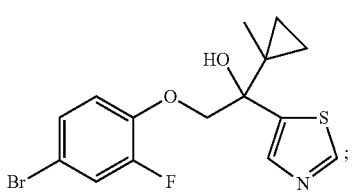

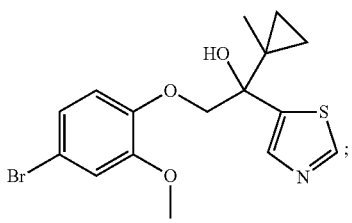

-continued
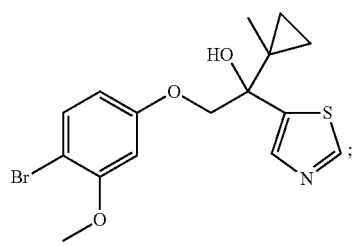
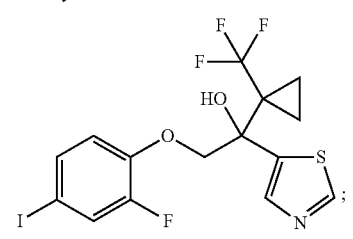
-continued
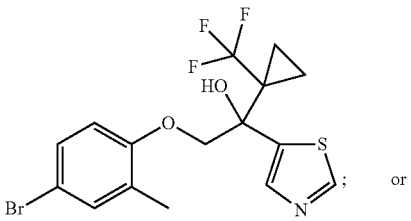
or
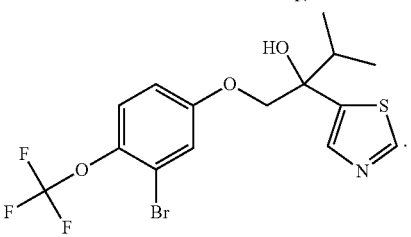
* * * * *